(12) United States Patent
Fujita et al.

(10) Patent No.: US 11,937,931 B2
(45) Date of Patent: Mar. 26, 2024

(54) PHYSICAL CONDITION DETERMINATION DEVICE, COMPUTER PROGRAM, AND RECORDING MEDIUM

(71) Applicant: DELTA KOGYO CO., LTD., Aki-gun (JP)

(72) Inventors: Etsunori Fujita, Higashihiroshima (JP); Yumi Ogura, Higashihiroshima (JP); Yoshika Nobuhiro, Aki-gun (JP)

(73) Assignee: DELTA KOGYO CO., LTD., Aki-gun (JP)

( * ) Notice: Subject to any disclaimer, the term of this patent is extended or adjusted under 35 U.S.C. 154(b) by 296 days.

(21) Appl. No.: 17/431,028

(22) PCT Filed: Jan. 15, 2020

(86) PCT No.: PCT/JP2020/001107
§ 371 (c)(1),
(2) Date: Aug. 13, 2021

(87) PCT Pub. No.: WO2020/166260
PCT Pub. Date: Aug. 20, 2020

(65) Prior Publication Data
US 2022/0117530 A1    Apr. 21, 2022

(30) Foreign Application Priority Data
Feb. 14, 2019 (JP) ................................. 2019-024065

(51) Int. Cl.
*A61B 5/18* (2006.01)
*A61B 5/0245* (2006.01)
(Continued)

(52) U.S. Cl.
CPC .............. *A61B 5/18* (2013.01); *A61B 5/0245* (2013.01); *A61B 5/11* (2013.01); *B60T 17/18* (2013.01); *B60K 28/02* (2013.01)

(58) Field of Classification Search
CPC ........... A61B 5/18; A61B 5/0245; A61B 5/11; A61B 5/02108; A61B 5/7282; B60K 28/02; G16H 50/30
See application file for complete search history.

(56) References Cited

U.S. PATENT DOCUMENTS

| | | | | |
|---|---|---|---|---|
| 4,404,974 A | * | 9/1983 | Titus | ...................... A61B 5/021 600/509 |
| 7,664,606 B2 | * | 2/2010 | Suzuki | ................. A61B 5/4041 702/19 |

(Continued)

FOREIGN PATENT DOCUMENTS

| | | |
|---|---|---|
| JP | 2006-34803 A | 2/2006 |
| JP | 2011-167362 A | 9/2011 |

(Continued)

OTHER PUBLICATIONS

International Search Report dated Mar. 17, 2020 in PCT/JP2020/001107 filed on Jan. 15, 2020, 2 pages.

*Primary Examiner* — John A Tweel, Jr.
(74) *Attorney, Agent, or Firm* — Oblon, McClelland, Maier & Neustadt, L.L.P.

(57) ABSTRACT

The occurrence of a sudden change in physical condition is detected. In a physical condition determination device 100, a heart rate-relate index calculation unit 110 specifies an appearance time of a sign of a sudden change in heart rate, from a time-series waveform of an index corresponding to a variation in the heart rate (heart rate-related index) and a blood pressure-related index calculation unit 120 specifies an appearance time of a sign of a sudden change in blood pressure, from a time-series waveform of an index corresponding to a variation in the blood pressure (blood pressure-related index). A physical condition sudden change determination unit 130 determines that a sudden change in physical condition (physical condition sudden change) has occurred in a case where these appearance times are both within a predetermined time. This enables the determination in which the sudden change in the heart rate and the sudden change in the blood pressure are taken into consideration, to enable the detection of the physical condition sudden change.

9 Claims, 17 Drawing Sheets

(51) Int. Cl.
*A61B 5/11* (2006.01)
*B60K 28/02* (2006.01)
*B60T 17/18* (2006.01)

(56) References Cited

U.S. PATENT DOCUMENTS

| | | | |
|---|---|---|---|
| 8,430,822 B2* | 4/2013 | Inoue | A61B 5/02225 600/490 |
| 8,597,185 B2* | 12/2013 | Pipke | G16H 50/50 706/26 |
| 9,144,402 B2* | 9/2015 | Fujita | A61B 5/6887 |
| 2006/0025698 A1 | 2/2006 | Nakagawa et al. | |
| 2013/0030256 A1 | 1/2013 | Fujita et al. | |
| 2018/0296152 A1 | 10/2018 | Fujita et al. | |
| 2022/0354374 A1* | 11/2022 | Fujita | A61B 5/02438 |

FOREIGN PATENT DOCUMENTS

| | | |
|---|---|---|
| JP | 2012-179202 A | 9/2012 |
| JP | 2016-97219 A | 5/2016 |
| JP | 2017-64364 A | 4/2017 |

* cited by examiner

DETERMINE THAT LOAD ON HEART FUNCTION IS LARGE IF PSD RATIO IS 2 OR MORE

PHYSICAL CONDITION DETERMINATION DEVICE, COMPUTER PROGRAM, AND RECORDING MEDIUM

TECHNICAL FIELD

The present invention relates to a physical condition determination device that determines the physical condition of a person using a biosignal, a computer program, and a recording medium.

BACKGROUND ART

Patent Document 1, Patent Document 2, and so on disclose a device having a means that finds a frequency time-series waveform from a time-series waveform of a biosignal that is mainly cardiocirculatory vibration collected from the upper body of a person, further finds a frequency-gradient time-series waveform, and frequency-analyzes these to determine the state of the person. In Patent Document 1, in the frequency analysis, power spectra of respective frequencies corresponding to predetermined function regulation signal, fatigue reception signal, and activity regulation signal belonging to the ULF band (ultra low-frequency band) to the VLF band (very low-frequency band) are found. Then, the state of the person is determined from time-series variations of the respective power spectra. Since the fatigue reception signal indicates a progress degree of fatigue in a normal active state, additionally comparing the degrees of dominance of the power spectra of the function regulation signal and the activity regulation signal enables to determine the state of the person (a relaxed state, a fatigued state, a sympathetic dominant state, a parasympathetic dominant state, or the like).

In Patent Document 2, a function regulation signal, a fatigue reception signal, and an activity regulation signal belonging to the ULF band (ultra low-frequency band) to the VLF band (very low-frequency band) are used as in Patent Document 1, but in Patent Document 2, distribution ratios of frequency components corresponding to these three signals to the total value 100 of power spectra of the frequency components are found in a time-series manner, and the state of the person is determined using time-series variations of the distribution ratios.

The arts of Patent Documents 1 and 2 are both based on the following findings. Specifically, the homeostasis of a person is maintained by fluctuation, and its frequency band is in the ULF band and the VLF band. On the other hand, in atrial fibrillation which is one of the heart diseases, it is said that a frequency at which the characteristic of the fluctuation of the cardiocirculatory system changes is 0.0033 Hz, and by capturing a variation in the fluctuation near 0.0033 Hz, it is possible to obtain information regarding homeostasis (see Non-patent Document 1). It is also said that a frequency band near 0.0033 Hz or lower and a frequency band near 0.0053 Hz are mainly associated with thermoregulation, and a frequency band of 0.01 to 0.04 Hz is associated with autonomic nervous control. When a frequency-gradient time-series waveform for use in the calculation of fluctuations of these low frequencies included in a biosignal was actually found and was frequency-analyzed, it was confirmed that there were a fluctuation of lower than 0.0033 Hz, namely, 0.0017 Hz and a fluctuation of near 0.0033 Hz, namely, in a band around 0.0035 Hz, and besides these two, there was a fluctuation in a frequency band around 0.0053 Hz.

The 0.0035 Hz signal (fatigue reception signal) is a fluctuation for maintaining the homeostasis by adapting to externally input stress and this indicates a progress degree of fatigue in a normal active state, the 0.0053 Hz signal (activity regulation signal) is a signal where a degree of the influence of the control of the endocrine system hormone in the active state appears, the signal of 0.0017 Hz lower than 0.0033 Hz (function regulation signal) is a signal controlling a change in physical condition and a decline in physical function, and these three signals in the aforesaid frequency bands work as a thermoregulatory function by interacting with one another. Therefore, the use of time-series variations and distribution ratios of power spectra of these signals enables the determination of the state of a person.

PRIOR ART DOCUMENT

Patent Document

Patent Document 1: Japanese Patent Application Laid-open No. 2011-167362
Patent Document 2: Japanese Patent Application Laid-open No. 2012-179202

Non-Patent Document

Non-patent Document 1: "Development of the measurement method of the prediction of sleep by finger plethysmogram data", FUJITA Etsunori et al., Ergonomics, Vol. 41, No. 4, 203-212, 2005

SUMMARY OF THE INVENTION

Problems to Be Solved by the Invention

The means disclosed in Patent Documents 1 and 2 use, as the biosignal, a pulse wave that is vibration generated on the body surface of the back of a person (dorsal body surface pulse wave) and detect it in a non-constraining manner, and these means are excellent in obtaining biological information, in particular, during driving.

A person may experience a sudden change in physical condition, for example, suddenly get pale, feel sick, or fall unconscious while driving or after given a load of exercise such as driving. As described above, the arts of Patent Documents 1 and 2 are effective for detecting a change in the biological state such as a hypnagogic symptom phenomenon and an imminent sleep phenomenon accompanying the progress of fatigue, but they do not disclose any specific method for detecting a sudden change in physical condition.

The present invention was made in consideration of the above and has an object to provide a suitable art for detecting the occurrence of a sudden change in physical condition.

Means for Solving the Problems

As a result of studious studies for solving the above problem, the present inventor has focused on the following points. Specifically, the aforesaid frequency-gradient time-series waveform found through the processing of the time-series waveform of the biosignal and the aforesaid time-series waveforms of the distribution ratios of the function regulation signal, the fatigue reception signal, and the activity regulation signal found from the frequency-gradient time-series waveform are all information regarding a variation in heart rate. When the physical condition suddenly changes, a sudden change in an index related to the variation in heart rate naturally occurs, and in addition, blood pressure also suddenly changes. Therefore, the present inventor thought that by also detecting the sudden change in the blood pressure from the dorsal body surface pulse wave as well as the variation in the heart rate, it is possible to determine that the sudden change in the physical condition has occurred when the two different indexes vary in different manners from those in the normal state, and has completed the present invention.

Specifically, a physical condition determination device of the present invention is a physical condition determination device which determines a physical condition of a person by analyzing a biosignal collected by a biosignal measurement device which is disposed in contact with a back of the person and captures, in a non-constraining manner, the biosignal propagated through a body surface of the back, the physical condition determination device including:

a heart rate-related index calculation unit which finds a time-series waveform of an index corresponding to a variation in heart rate from a time-series waveform of the biosignal;

a blood pressure-related index calculation unit which finds a time-series waveform of an index corresponding to a variation in blood pressure from the time-series waveform of the biosignal; and a physical condition sudden change determination unit which specifies a preset time zone in which the time-series waveform obtained from the heart rate-related index calculation unit presents a predetermined waveform variation, as an appearance time of a sign of a sudden change in the heart rate, specifies a preset time zone in which the time-series waveform obtained from the blood pressure-related index calculation unit presents a predetermined waveform variation, as an appearance time of a sign of a sudden change in the blood pressure, and determines that a sudden change in the physical condition has occurred in a case where the appearance time of the sign of the sudden change in the heart rate and the appearance time of the sign of the sudden change in the blood pressure are within a predetermined time range.

Preferably, the heart rate-related index calculation unit includes: a frequency-gradient time-series waveform calculation unit which, after finding a frequency time-series waveform from the time-series waveform of the biosignal, finds a frequency-gradient time-series waveform in every predetermined time range from the frequency time-series waveform; and a distribution ratio time-series waveform calculation unit which extracts, from the frequency-gradient time-series waveform, frequency components belonging to a ULF band to a VLF band corresponding to a function regulation signal having a frequency lower than a frequency at which a fluctuation characteristic of a cardiocirculatory system changes, a fatigue reception signal higher in frequency than the function regulation signal, and an activity regulation signal higher in frequency than the fatigue reception signal, and finds time-series waveforms of distribution ratios of the frequency components.

Preferably, the physical condition sudden change determination unit specifies, as the appearance time of the sign of the sudden change in the heart rate, a time zone in which a point appears at which the waveforms of the function regulation signal, the fatigue reception signal, and the activity regulation signal all belong to a predetermined distribution ratio range and the distribution ratio of the activity regulation signal is the lowest, and thereafter a point appears at which the distribution ratio of the activity regulation signal becomes higher than the distribution ratios of the function regulation signal and the fatigue reception signal.

Preferably, the blood pressure-related index calculation unit includes: a systolic blood pressure-related index calculation unit which finds a time-series waveform of a systolic blood pressure-related index by using peak values of the time-series waveform of the biosignal; and a diastolic blood pressure-related index calculation unit which finds a time-series waveform of a diastolic blood pressure-related index by using bottom values of the time-series waveform of the biosignal.

Preferably, the systolic blood pressure-related index calculation unit finds the time-series waveform of the systolic blood pressure-related index by using a gradient of the peak values in every predetermined time range, the diastolic blood pressure-related index calculation unit finds the time-series waveform of the diastolic blood pressure-related index by using a gradient of the bottom values in every predetermined time range, and the physical condition sudden change determination unit specifies, as the appearance time of the sign of the sudden change in the blood pressure, a time zone in which the time-series waveform of the systolic blood pressure-related index found using the gradient of the peak values in every predetermined time range and the time-series waveform of the diastolic blood pressure-related index found using the gradient of the bottom values in every predetermined time range cross each other and a point appears at which a value of the systolic blood pressure-related index is smaller than a value of the diastolic blood pressure-related index.

Preferably, the physical condition determination device further includes a heart function determination unit which determines whether or not a load on a heart function is large, and the physical condition sudden change determination unit determines that the sudden change in the physical condition has occurred in a case where the heart function determination unit determines that the load on the heart function is large as well as the appearance time of the sign of the sudden change in the heart rate and the appearance time of the sign of the sudden change in the blood pressure are within the predetermined time range.

Preferably, the heart function determination unit frequency-analyzes the frequency-gradient time-series waveform found at the time of the physical condition determination by the heart rate-related index calculation unit, compares the frequency analysis with a frequency analysis of a frequency-gradient time-series waveform found in advance at a resting time, and determines that the load on the heart function is large in a case where a ratio of a power spectrum value of a dominant frequency at the time of the physical condition determination to a power spectrum value of a dominant frequency at the resting time is equal to a predetermined value or more.

Further, a computer program of the present invention is a computer program which causes a computer as a physical condition determination device to execute a procedure for determining a physical condition of a person by analyzing a biosignal obtained from a biosignal measurement device which is disposed in contact with a back of the person and captures the biosignal propagated through a body surface of the back, the computer program causing the computer to execute:

a heart rate-related index calculation procedure for finding a time-series waveform of an index corresponding to a variation in heart rate from a time-series waveform of the biosignal;

a blood pressure-related index calculation procedure for finding a time-series waveform of an index corresponding to a variation in blood pressure from the time-series waveform of the biosignal; and a physical condition sudden change determination procedure for specifying a preset time zone in which the time-series waveform obtained through the execution of the heart rate-related index calculation procedure presents a predetermined waveform variation, as an appearance time of a sign of a sudden change in the heart rate, specifying a preset time zone in which the time-series waveform obtained through the execution of the blood pressure-related index calculation procedure presents a predetermined waveform variation, as an appearance time of a sign of a sudden change in the blood pressure, and determining that a sudden change in the physical condition has occurred in a case where the appearance time of the sign of the sudden change in the heart rate and the appearance time of the sign of the sudden change in the blood pressure are within a predetermined time range.

Preferably, the computer program causes the computer to further execute a heart function determination procedure for determining whether or not a load on a heart function is large, and in the physical condition sudden change determination procedure, it is determined that the sudden change in the physical condition has occurred in a case where the load on the heart function is determined as large through the execution of the heart function determination procedure as well as the appearance time of the sign of the sudden change in the heart rate and the appearance time of the sign of the sudden change in the blood pressure are within the predetermined time range.

Further, the present invention provides a computer-readable recording medium in which the aforesaid computer program is recorded, the computer program causing the computer to function as the physical condition determination device by causing the computer to execute the procedure for determining the physical condition of a person by analyzing the biosignal obtained from the biosignal measurement device which is disposed in contact with the back of the person and captures the biosignal propagated through the body surface of the back.

Effect of the Invention

The present invention is configured to specify the appearance time of the sign of the sudden change in the heart rate, from the time-series waveform of the index corresponding to the variation in the heart rate (heart rate-related index) and specifies the appearance time of the sign of the sudden change in the blood pressure, from the time-series waveform of the index corresponding to the variation in the blood pressure (blood pressure-related index), and determine that the sudden change in the physical condition (physical condition sudden change) has occurred in the case where both of the appearance times are within the predetermined time range. This enables the determination in which the sudden change in the heart rate and the sudden change in the blood pressure are taken into consideration, enabling the detection of the physical condition sudden change.

It is preferable to additionally determine whether or not the load on the heart function is larger than that at a resting time. Typically, when the physical condition sudden change has occurred, the load on the heart function is also large. Therefore, not only specifying the sudden change in the heart rate and the sudden change in the blood pressure but also determining whether or not the load on the heart function is large enables the more accurate detection of the occurrence of the physical condition sudden change.

DESCRIPTION OF EMBODIMENT

Figure 1:
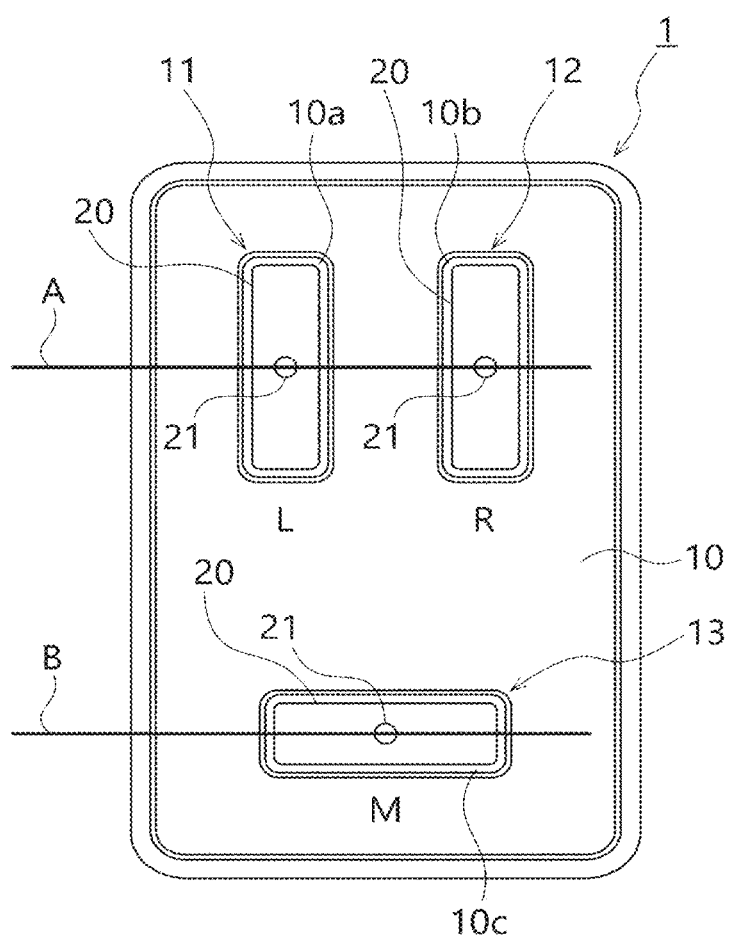
FIG. 1 is a plan view of a biosignal measurement device used in an embodiment of the present invention.

The present invention will be hereinafter described in more detail based on an embodiment of the present invention illustrated in the drawings. In the present invention, a biosignal propagated through the dorsal body surface of a person (dorsal body surface pulse wave) is used. As described above, the dorsal body surface pulse wave is vibration (including vibration transmitted as sound) that is generated when blood flowing in the ventricles or the atriums in atrial or ventricular systoles or diastoles collides with valves or myocardial inner walls or when the blood flowing in the aorta presses vascular walls, and transmitted to the body surface.

Figure 2:
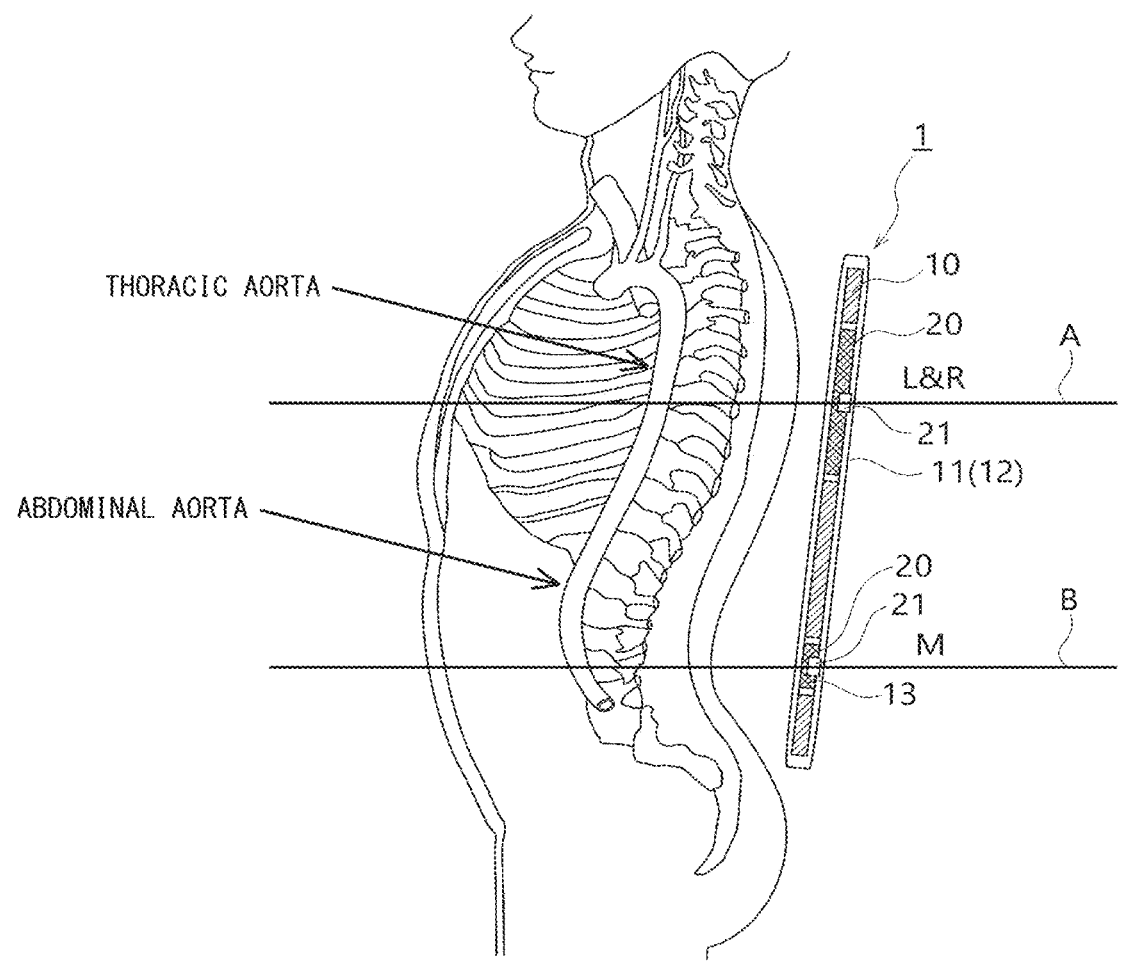
FIG. 2 is a vertical sectional view illustrating arrangement positions of a left upper part biosignal detection unit (L), a right upper part biosignal detection unit (R), and a lower part biosignal detection unit (M) in relation to the body of a person when the biosignal measurement device is disposed on the back side of the person.
Figure 3:
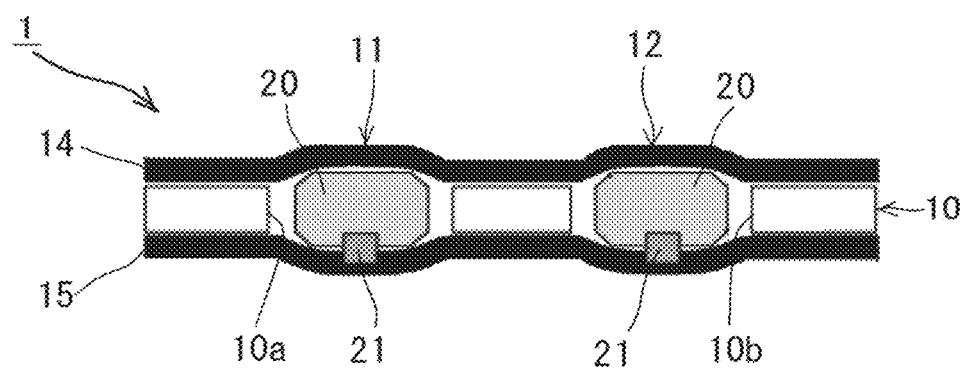
FIG. 3 is a partial sectional view of the biosignal measurement device.

Preferably, the biosignal measurement device for collecting the dorsal body surface pulse wave can be used while assembled in a measurement chair or bed, a seat of a vehicle driver seat, or the like and is capable of collecting the biosignal without constraining an arm, a hand, a finger, or the like. FIG. 1 to FIG. 3 illustrate the biosignal measurement device 1 used in this embodiment. The biosignal measurement device 1 includes three biosignal detection units, namely, a left upper part biosignal detection unit 11, a right upper part biosignal detection unit 12, and a lower part biosignal detection unit 13 which are provided in a base member 10.

The base member 10 is formed of a plate-shaped body having an area large enough to include the three biosignal detection units 11 to 13 and cover a range including the chest to the abdomen of the person. Its material is preferably a flexible synthetic resin or the like giving little uncomfortable feeling to the person when the back of the person abuts thereon, and is more preferably a bead foam. Thin films of beads forming the bead foam sensitively respond to the biosignal-based microvibration of the body surface to vibrate, so that the biosignal is easily propagated to the biosignal detection units 11 to 13.

In the state in which the base member 10 is disposed along the back of the person, above (on the shoulder side of) a diaphragm-corresponding position corresponding to the position of the diaphragm of the person, two detection unit placement holes 10a, 10b are formed at a position corresponding to the position of the heart (near the line indicated by reference sign A in FIG. 1 and FIG. 2), and under (on the waist side of) the diaphragm-corresponding position, one detection unit placement hole 10c is formed at a position corresponding to the position of the waist (near the line indicated by reference sign B in FIG. 1 and FIG. 2). The two detection unit placement holes 10a, 10b on the upper side are provided at a predetermined interval on the left and right of a backbone-corresponding position corresponding to the position of the backbone of the person. Further, the two detection unit placement holes 10a, 10b on the upper side are substantially in a vertically-long rectangular shape that is longer in the up-down direction, and the detection unit placement hole 10c on the lower side is substantially in a laterally-long rectangular shape that is longer in the left-right direction. To enable the capturing of biosignals of a range corresponding to the lungs and the heart, the two detection unit placement holes 10a, 10b on the upper side are vertically long, and to enable the capturing of abdominal information that is based on the activity of the left and right lungs and is transmitted through the diaphragm, the detection unit placement hole 10c on the lower side is laterally long. This corresponds to the shapes and the arrangement directions of the biosignal detection units 11 to 13.

The biosignal detection units 11 to 13 each have a three-dimensional knitted fabric 20 and an acoustic sensor 21 constituted by a microphone. The three-dimensional knitted fabric 20 is formed of a pair of ground knitted fabrics disposed apart from each other and connecting yarns connecting the ground knitted fabrics as is disclosed in, for example, Japanese Patent Application Laid-open No. 2002-331603. For example, the ground knitted fabrics each can be formed to have a flat knitted fabric structure (fine meshes) continuous both in a wale direction and a course direction using yarns of twisted fibers or to have a knitted fabric structure having honeycomb (hexagonal) meshes. The connecting yarns impart predetermined rigidity to the three-dimensional knitted fabric so that one of the ground knitted fabrics and the other ground knitted fabric are kept at a predetermined interval. Therefore, applying tension in a planar direction makes it possible to cause string vibration of the yarns of the facing ground knitted fabrics forming the three-dimensional knitted fabric or of the connecting yarns connecting the facing ground knitted fabrics. Accordingly, cardio-vascular sound/vibration being a biosignal causes the string vibration and is propagated in the planar direction of the three-dimensional knitted fabric.

The three-dimensional knitted fabrics 20 forming the biosignal detection units 11 to 13 are formed in a substantially rectangular shape corresponding to the aforesaid detection unit placement holes 10a to 10c. Then, films 14, 15 are stacked on both surfaces of the base member 10 to cover the front surfaces and the rear surfaces of the three-dimensional knitted fabrics 20. The films 14, 15 each may have a size corresponding to each of the detection unit placement holes 10a to 10c, or the films 14, 15 each may have a size that can cover, by itself, all the three detection unit placement holes 10a to 10c. Consequently, the detection unit placement holes 10a to 10c become resonance boxes to have a function of amplifying weak biosignals.

Figure 4:
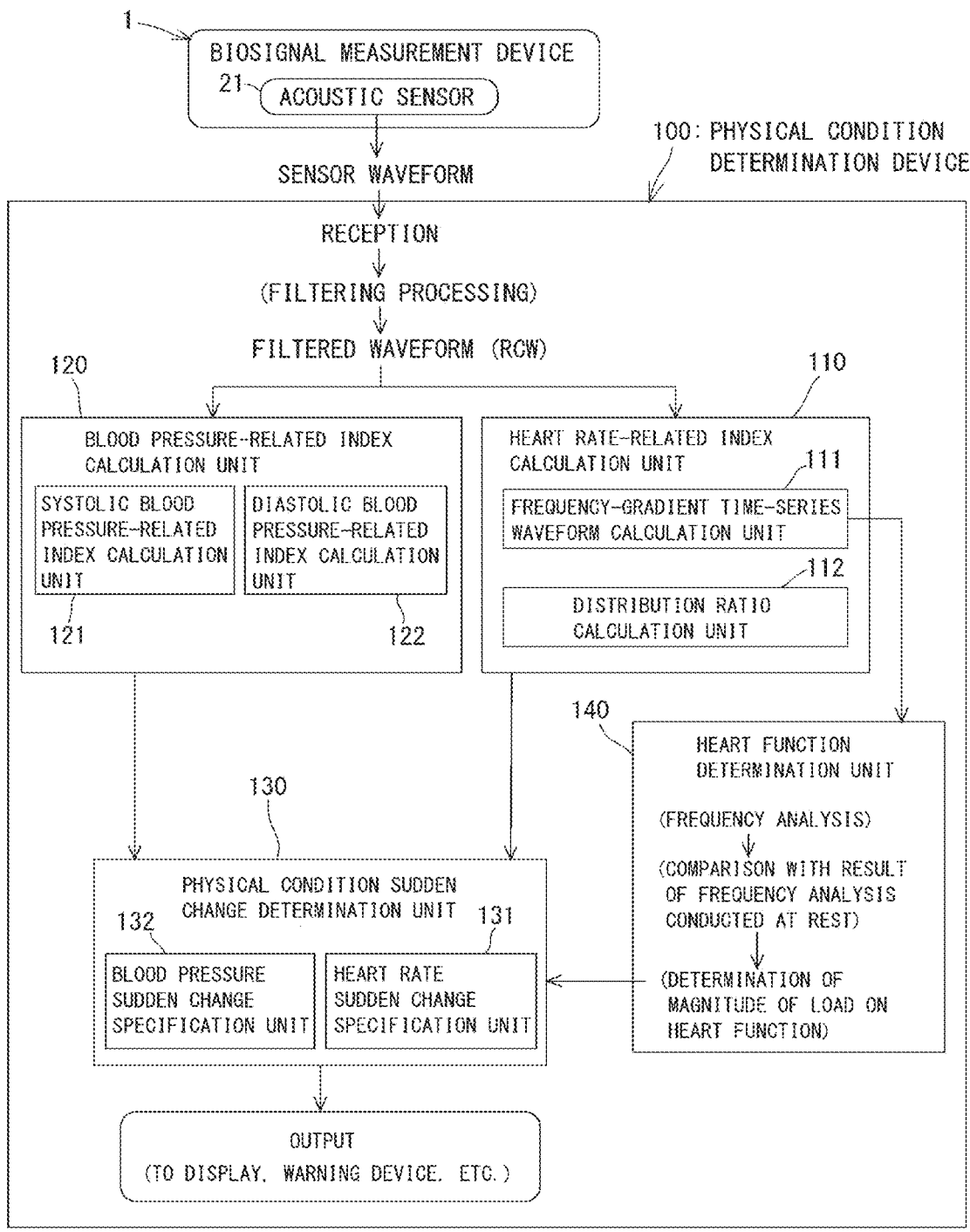
FIG. 4 is an explanatory block diagram of the configuration of a physical condition determination device according to the embodiment of the present invention.

Next, the configuration of the physical condition determination device 100 of this embodiment will be described based on FIG. 4. The physical condition determination device 100 is constituted by a computer (including a personal computer, a microcomputer incorporated in the device, and the like), and a computer program causing the computer to execute a procedure for determining a physical condition is stored in a storage unit (including not only a built-in recording medium such as a hard disk of the computer (physical condition determination device 100) but also any of various removable recording mediums and a recording medium of another computer connected through a communication means). By executing the procedure for determining a physical condition, the computer constitutes the physical condition determination device 100 having functions as a heart rate-related index calculation unit 110, a blood pressure-related index calculation unit 120, a physical condition sudden change determination unit 130, and a heart function determination unit 140. Further, the computer program causing the execution of the procedure for determining a physical condition can be implemented by an electronic circuit including one storage circuit or more in which the computer program is incorporated.

Further, the computer program can be provided in a state of being stored in a recording medium. The recording medium storing the computer program may be a non-transitory recording medium. The non-transitory recording medium is not limited, and examples thereof are recording media such as a flexible disk, a hard disk, CD-ROM, MO (magneto-optical disk), DVD-ROM, and a memory card. Further, the computer program can be transmitted to the computer through a communication line to be installed therein.

Figure 5:
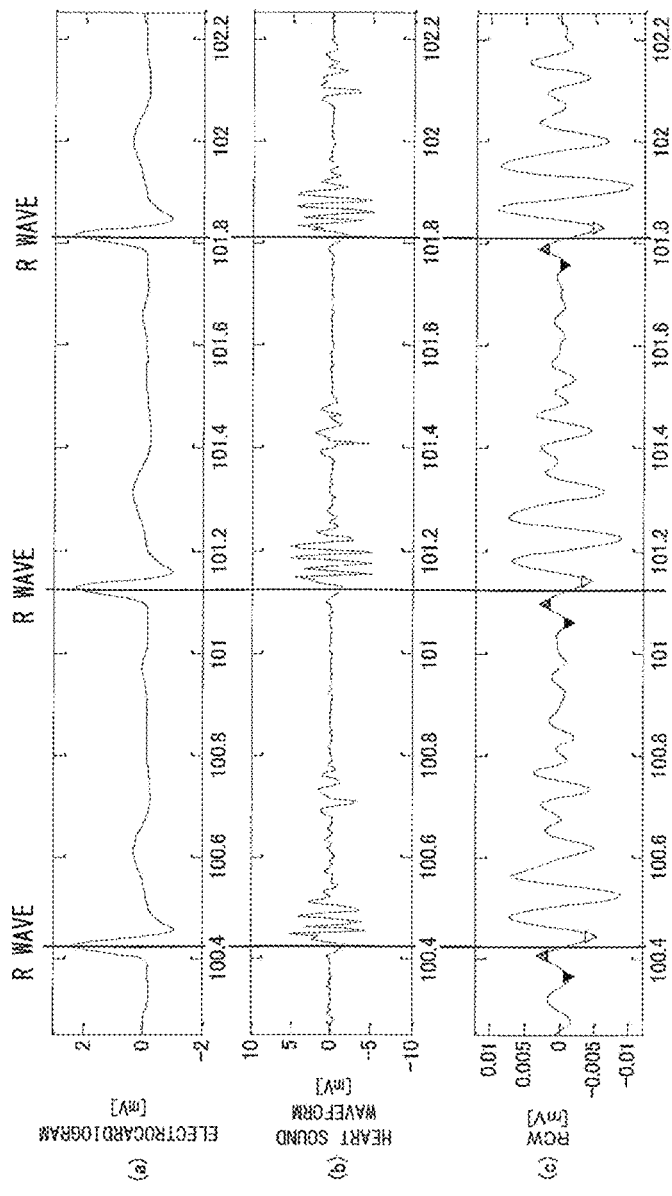
FIGS. 5(a) to (c) are charts illustrating an electrocardiogram waveform (a), a heart sound waveform (b), and a waveform (RCW) (c) resulting from the filtering of a biosignal obtained from the biosignal measurement device.

The heart rate-related index calculation unit 110 and the blood pressure-related index calculation unit 120 both use a time-series waveform of a biosignal obtained from the acoustic sensor 21 of the biosignal measurement device 1 (hereinafter, referred to as a "sensor waveform")), but preferably use not the sensor waveform itself but a time-series waveform resulting from the filtering of the sensor waveform with a band-pass filter whose center frequency is around 20 Hz, more preferably, a band-pass filter of a 10 to 30 Hz frequency band. The filtering converts the sensor waveform to a filtered waveform of 10 to 30 Hz (waveform in FIG. 5(c) (hereinafter, referred to as "RCW"). A standard range of heart rate is around 1 to 1.5 Hz, and it is seen that, in RCW, waveform components with a relatively large total amplitude appear at a cycle of about one second, which means that the cardiac cycle is manifested in RCW. This is obvious from the comparison with the waveform of the electrocardiogram in FIG. 5(a) and the waveform of the phonocardiogram in FIG. 5(b).

The heart rate-related index calculation unit 110 finds a time-series waveform of an index corresponding to a variation in heart rate from the time-series waveform ("RCW" in this embodiment) of the biosignal. The heart rate-related index calculation unit 110 of this embodiment includes a frequency-gradient time-series waveform calculation unit 111 and a distribution ratio calculation unit 112. The frequency-gradient time-series waveform calculation unit 111 finds a frequency time-series waveform from RCW and finds a frequency-gradient time-series waveform in every predetermined time range, from the frequency time-series waveform.

More specifically, the frequency-gradient time-series waveform is obtained by the method disclosed in Patent Documents 1 and 2. Specifically, in RCW, positive-to-negative change points (zero-cross points) are found, are divided into segments in, for example, every five seconds, reciprocals of time intervals between the zero-cross points of the time-series waveform included in the five-second period are found as individual frequencies f, and an average value of the individual frequencies fm in the five-second period is adopted as a value of a frequency F in the relevant five-second period. Then, the frequencies F obtained every five seconds are plotted in a time-series manner, whereby a time-series waveform of a frequency variation is found. Next, in the time-series waveform of the frequency variation, time windows overlapping with each other by a predetermined overlap time (for example, eighteen seconds) and each having a predetermined time width (for example, 180 seconds) are set, a frequency gradient in each time window is found by the least squares method, and a time-series waveform of the gradient is output. The heart rate-related index calculation unit 110 repeats this calculation (moving calculation) in sequence to output a time-series variation in the frequency gradient as the frequency-gradient time-series waveform. The dorsal body surface pulse wave is a biosignal mainly including the control state of the heart being the central nervous system, that is, a biosignal including information on the state of the sympathetic innervation of arteries and the appearance of the sympathetic nervous system and the parasympathetic nervous system, and the frequency-gradient time-series waveform found by the zero-cross method is an index corresponding to a variation in heart rate.

The distribution ratio calculation unit 112 first frequency-analyzes the frequency-gradient time-series waveform obtained from the frequency-gradient time-series waveform calculation unit 111 and extracts frequency components belonging to the ULF band to the VLF band corresponding to a function regulation signal whose frequency is lower than 0.0033 Hz which is a frequency at which the fluctuation characteristic of the cardiocirculatory system changes, a fatigue reception signal higher in frequency than the function regulation signal, and an activity regulation signal higher in frequency than the fatigue reception signal. Next, distribution ratios of these frequency components are found in a time-series manner. That is, ratios of the frequency components to the total value 1 of power spectra of the three frequency components are found as the distribution ratios in a time-series manner.

In this embodiment, a 0.0017 Hz frequency component is used as the function regulation signal, a 0.0035 Hz frequency component as the fatigue reception signal, and a 0.0053 Hz frequency component as the activity regulation signal, and the use of these frequency components is appropriate as described in "Background Art" section above. Note that the frequency components used as these signals can be adjusted depending on an individual difference or the like, and the function regulation signal can be adjusted within a range of less than 0.0033 Hz, preferably a range of 0.001 to 0.0027 Hz, the fatigue reception signal within a range of 0.002 to 0.0052 Hz, and the activation regulation signal within a range of 0.004 to 0.007 Hz.

The blood pressure-related index calculation unit 120 finds a time-series waveform of an index corresponding to a variation in blood pressure from the time-series waveform ("RCW" in this embodiment) of the biosignal. The blood pressure-related index calculation unit 120 of this embodiment includes a systolic blood pressure-related index calculation unit 121 which finds a time-series waveform of a systolic blood pressure-related index by using peak values of RCW and a diastolic blood pressure-related index calculation unit 122 which finds a time-series waveform of a diastolic blood pressure-related index by using bottom values of RCW. Further, to manifest a change tendency of the peak values or the bottom values, the systolic blood pressure-related index calculation unit 121 and the diastolic blood pressure-related index calculation unit 122 each find a gradient (rate) of the change of the peak values or the bottom values in a predetermined time range (for example, 180 seconds), and perform slide calculation with, for example, an eighteen-second overlap time, to find a change in a gradient of the peak values or the bottom values in sequence.

Here, in the later-described experimental examples, experiments were conducted in which, before and after given an exercise load by ten-minute running using a treadmill, each subject was seated in an automobile seat to whose seat back part the above-described biosignal measurement device 1 was attached, and his/her biosignal was detected. At the time of the experiments, an instantaneous heart rate monitor and a continuous blood pressure monitor were worn by each subject to also measure his/her instantaneous blood pressure and continuous blood pressure. In FIG. 10 to FIG. 15, the charts (c) each illustrate time-series waveforms of systolic blood pressure and diastolic blood pressure measured with the continuous blood pressure monitor, and the charts (d) each illustrate time-series waveforms of average values of the peak values and the bottom values of RCW in every 180-second period which are found with eighteen-second sliding. The comparison of these charts shows that the time-series waveform of the systolic blood pressure measured with the continuous blood pressure monitor presents a variation substantially corresponding to that of the time-series waveform of the peak average value calculated using RCW, and the time-series waveform of the diastolic blood pressure measured with the continuous blood pressure monitor presents a variation substantially corresponding to that of the time-series waveform of the bottom average value calculated using RCW.

Figure 6:
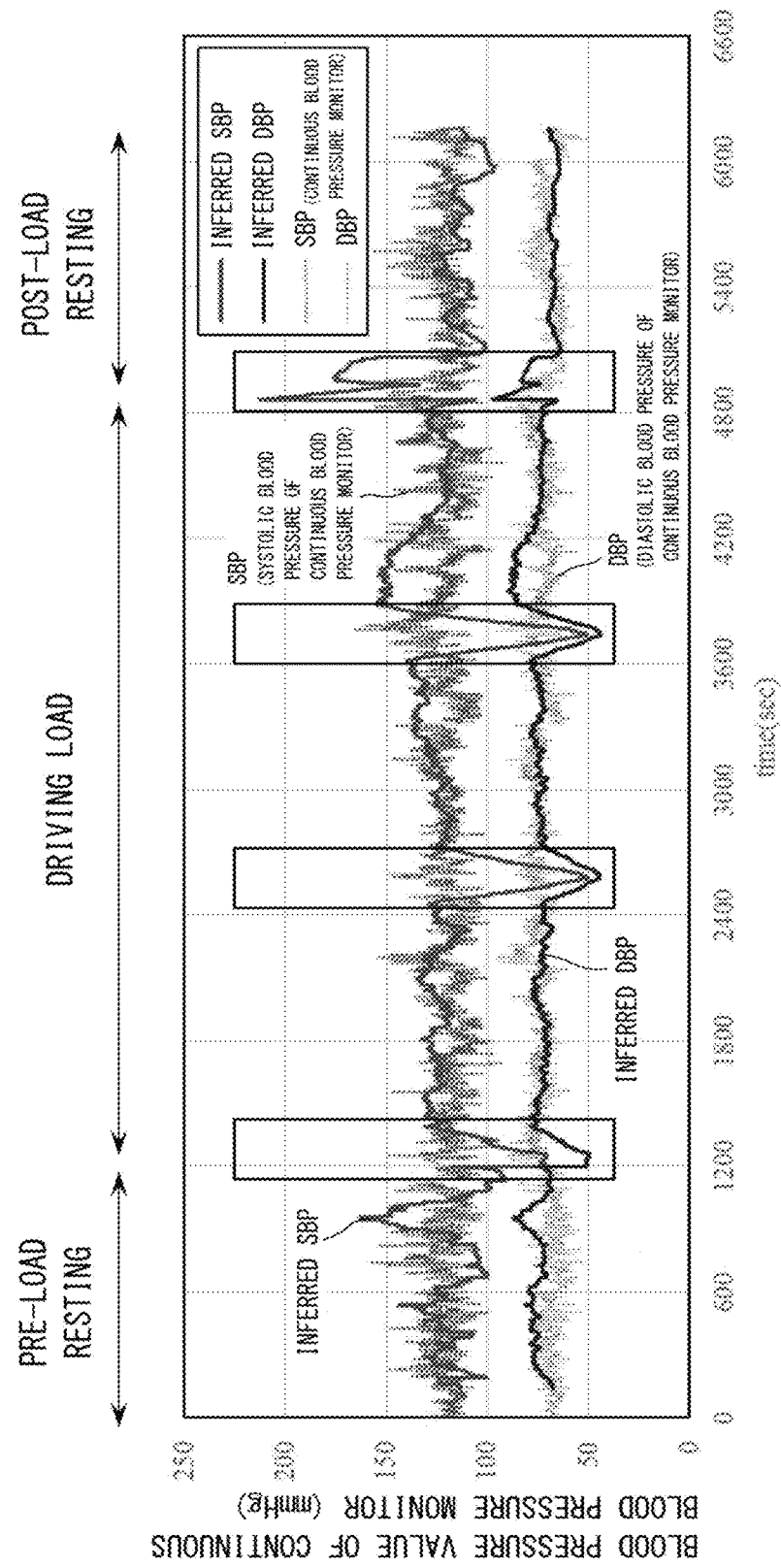
FIG. 6 is a chart illustrating an example of a correspondence relation between time-series waveforms of systolic blood pressure and diastolic blood pressure which are obtained from a continuous blood pressure monitor and time-series waveforms of average values of peak values and bottom values calculated using RCW.

Further, a biosignal was detected while a subject was seated in the automobile seat to whose seat back the biosignal measurement device 1 was attached, rested for twenty minutes, thereafter drove for sixty minutes, and then rested for twenty minutes, and time-series waveforms of average values of peak values and bottom values of RCW in each 180-second period were found with 180-second sliding. FIG. 6 illustrates the result of the comparison of the time-series waveforms with the continuous blood pressure monitor measured at the same time. In FIG. 6, "inferred SBP" is a waveform obtained when the average value of the peak values calculated using RCW is multiplied by a predetermined coefficient so that the waveform approximates the systolic blood pressure value of the continuous blood pressure monitor, and "inferred DBP" is a waveform obtained when the average value of the bottom values calculated using RCW is multiplied by a predetermined coefficient so that the waveform approximates the diastole blood pressure value of the continuous blood pressure monitor. From these graphs, it is seen that the time-series waveforms of the average values of the peak values and the bottom values of RCW well correspond to the time-series waveforms of the systolic blood pressure and the diastolic blood pressure obtained from the continuous blood pressure monitor.

Therefore, a gradient of the peak values of RCW found by the systolic blood pressure-related index calculation unit 121 and a gradient of the bottom values of RCW found by the diastolic blood pressure-related index calculation unit 122 are suitable as indexes indicating variation tendencies of the systolic blood pressure and the diastole blood pressure.

In the physical condition sudden change determination unit 130, the computer program causes the execution of a procedure functioning as a heart rate sudden change specification unit 131, causes the execution of a procedure functioning as a blood pressure sudden change specification unit 132, and thereafter, causes the execution of a procedure for determining a physical condition sudden change based on the execution results of the above two procedures.

Specifically, the heart rate sudden change specification unit 131 specifies a preset time zone in which the time-series waveform obtained from the heart rate-related index calculation unit 110 presents a predetermined waveform variation, as an appearance time of a sign of a sudden change in heart rate, and the blood pressure sudden change specification unit 132 specifies a preset time zone in which the time-series waveform obtained from the blood pressure-related index calculation unit 120 presents a predetermined waveform variation, as an appearance time of a sign of a sudden change in blood pressure. Next, in a case where the appearance time of the sign of the sudden change in the heart rate and the appearance time of the sign of the sudden change in the blood pressure are within a predetermined time range, the physical condition sudden change determination unit 130 determines that a sudden change in the physical condition (physical condition sudden change) has occurred. That is, in a case where the two indexes of the variation in the heart rate and the variation in the blood pressure present waveforms different from normal waveforms and they appear in substantially the same period (the predetermined time range), it is determined that the physical condition sudden change mentioned here has occurred.

Figure 7:
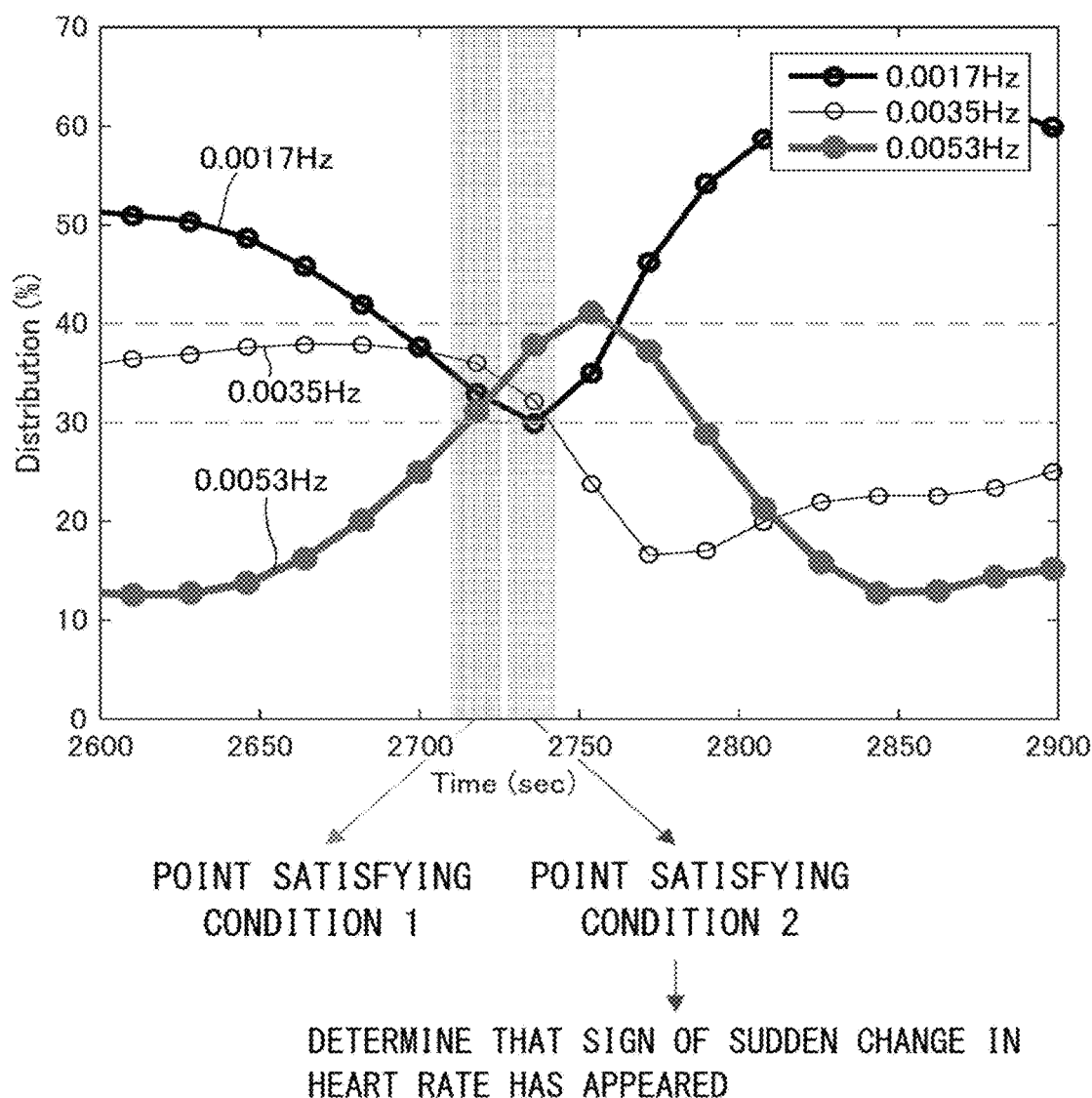
FIG. 7 is a chart for explaining how a heart rate sudden change specification unit specifies an appearance time of a sign of a sudden change in heart rate.

The heart rate sudden change specification unit 131 preferably specifies the appearance time of the sign of the sudden change in the heart rate, as follows. Specifically, it is determined whether or not a point appears at which the waveforms of the aforesaid function regulation signal, fatigue reception signal, and activity regulation signal which are found from the frequency-gradient time-series waveform by the distribution ratio calculation unit 112 all belong to a predetermined distribution ratio range, and in this case, the distribution ratio of the activity regulation signal is the lowest (condition 1), and thereafter a point appears at which the distribution ratio of the activity regulation signal becomes higher than the distribution ratios of the function regulation signal and the fatigue reception signal (condition 2), and if the condition 1 and the condition 2 are both satisfied, it is determined that the sign of the sudden change in the heart rate has appeared. For example, in FIG. 7, in the case where the distribution ratios of the three waveforms of the function regulation signal (0.0017 Hz), the fatigue reception signal (0.0035 Hz), and the activity regulation signal (0.0053 Hz) all belong to a 30 to 40% range, the distribution ratio of the activity regulation signal (0.0053 Hz) is the lowest at this instant, and at an instant immediately thereafter (eighteen seconds later in this embodiment), the distribution ratio of the activity regulation signal (0.0053 Hz) becomes the highest, it is determined that the sign of the sudden change in the heart rate has appeared. In this embodiment, since calculation points are plotted every eighteen seconds by the moving calculation as described above, a 30- to 40-second time zone including these two points is preferably specified as the appearance time of the sign of the sudden change in the heart rate.

In the slide calculation for finding the frequency-gradient time-series waveform, the 180-second windows preferably overlap with one another by eighteen seconds as in this embodiment. However, the present invention also includes a mode in which each of the time windows is set longer or shorter than 180 seconds and the overlap ratio is set to a different value in the calculation and the same method as above is used. Further, the time zone when the sign of the sudden change in heart rate should appear can be set longer or shorter than thirty to forty seconds depending on the set time window, the set overlap ratio, or the like. Further, there may be a case where the distribution ratio range, of the condition 1, in which the aforesaid signals should gather is preferably set to a range other than the 30 to 40% range. Further, since these conditions differ depending on each individual, the conditions can be set for each individual.

Figure 8:
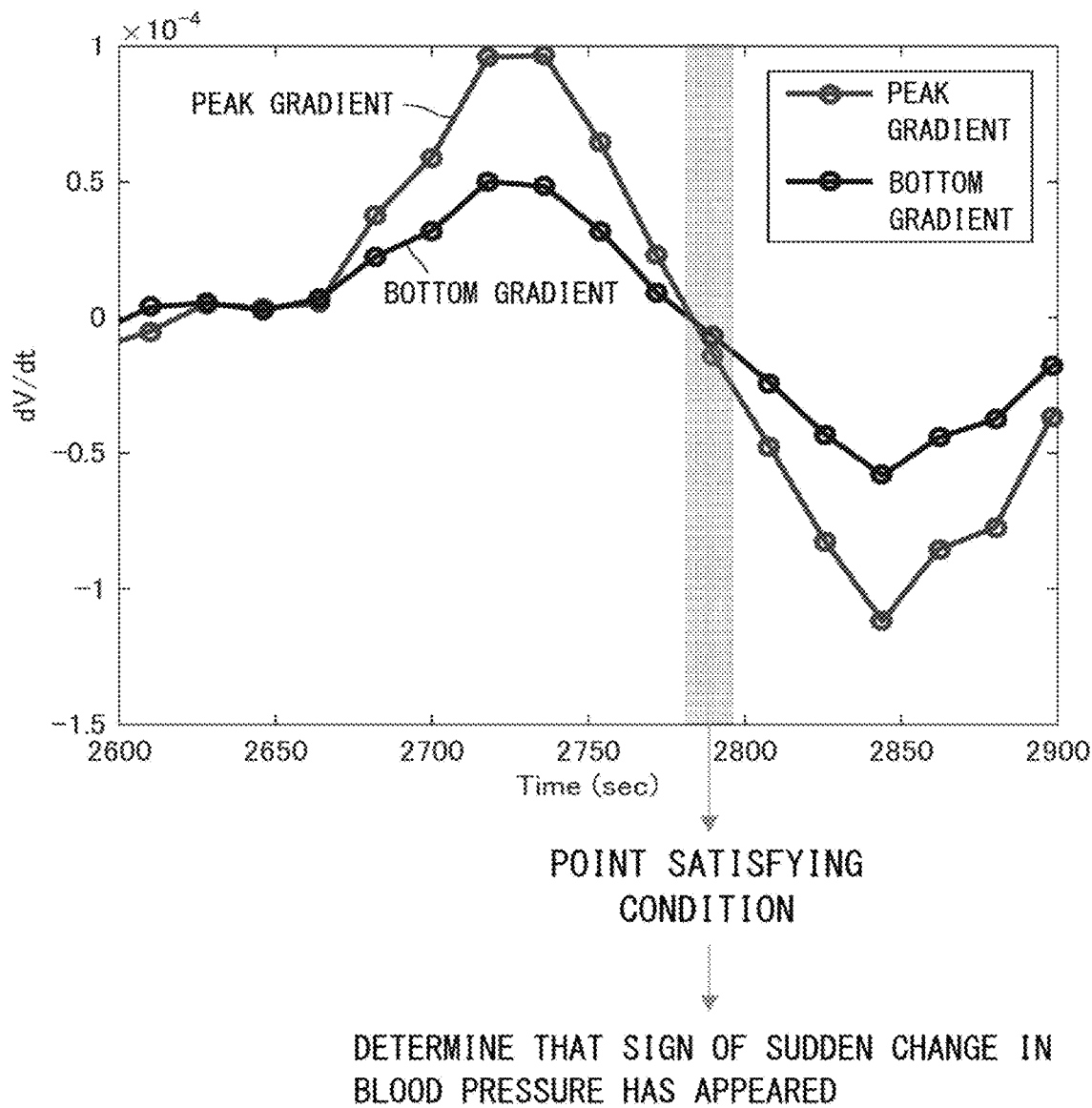
FIG. 8 is a chart for explaining how a blood pressure sudden change specification unit specifies an appearance time of a sign of a sudden change in blood pressure.

The blood pressure sudden change specification unit 132 preferably specifies the appearance time of the sign of the sudden change in the blood pressure as follows. Specifically, as illustrated in FIG. 8, a time zone in which the aforesaid time-series waveform of the systolic blood pressure-related index obtained from the systolic blood pressure-related index calculation unit 121 and the aforesaid time-series waveform of the diastolic blood pressure-related index obtained from the diastolic blood pressure-related index calculation unit 122 cross each other and a point appears at which a value of the systolic blood pressure-related index is smaller than a value of the diastolic blood pressure-related index is specified as the appearance time of the sign of the sudden change in the blood pressure. In this embodiment, since the calculation result is output every eighteen seconds as described above, whether or not the condition for the appearance time of the sign of the sudden change in the blood pressure is satisfied is determined every eighteen seconds, but this is only an example, and the blood pressure sudden change specification unit 132 may output the determination result at different time intervals depending on the set time and overlap ratio of the time windows, and so on of the slide calculation, similarly to the heart rate sudden change specification unit 131. Further, similarly to the above, the time window and the overlap ratio can be set appropriately for each individual.

The physical condition sudden change determination unit 130 compares the appearance time of the sign of the sudden change in the heart rate, which time is specified by the heart rate sudden change specification unit 131, and the appearance time of the sign of the sudden change in the blood pressure, which time is specified by the blood pressure sudden change specification unit 132, to finally determine whether or not the physical condition sudden change has occurred. In this embodiment, only in the case where the appearance time of the sign of the sudden change in the heart rate and the appearance time of the sign of the sudden change in the blood pressure are within the predetermined time range, it is determined that the physical condition sudden change has occurred. The predetermined time range mentioned here is preferably about 30 to about 100 seconds, though differing depending on each individual. Note that this predetermined time range can be set differently depending on the set time and overlap ratio of the time window, and so on of the slide calculation or depending on each individual.

Figure 9:
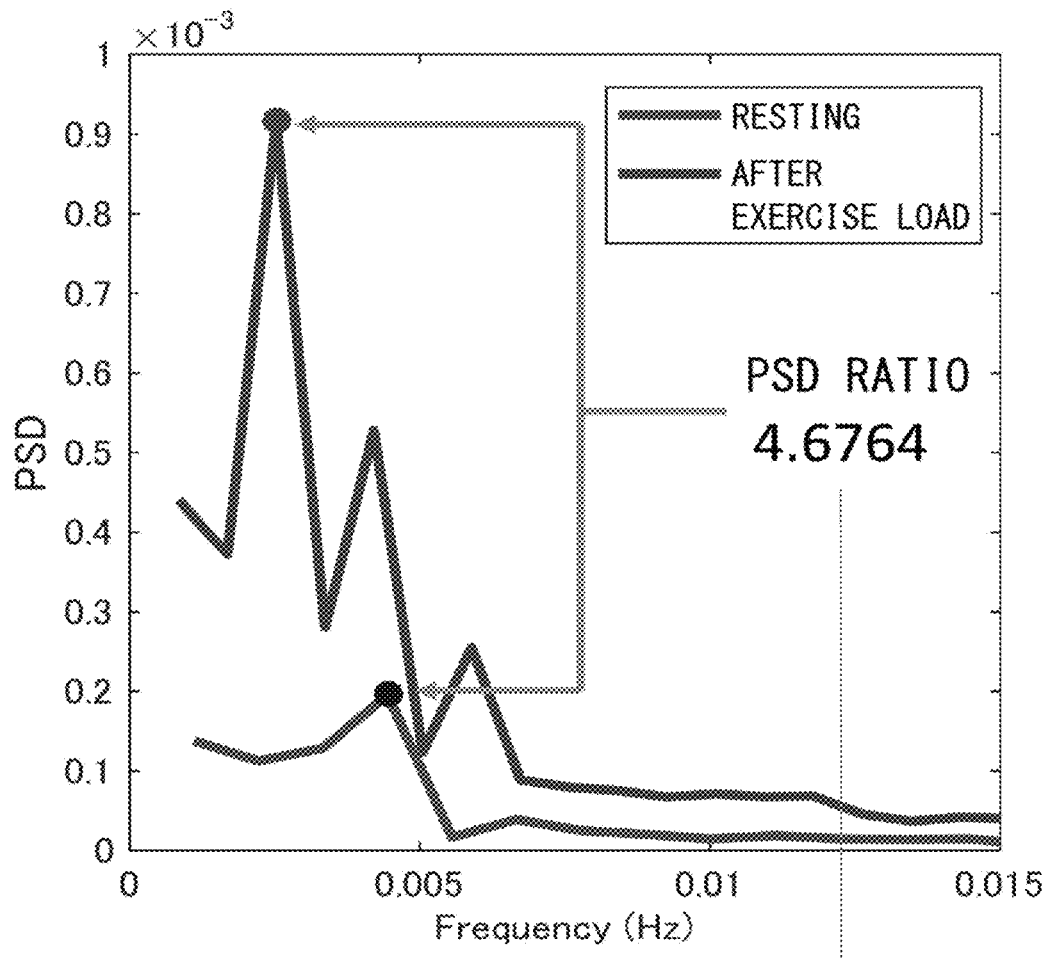
FIG. 9 is a chart for explaining how a heart function determination unit determines whether or not a load on a heart function is large.

The heart function determination unit 140 determines whether or not a load on the heart function is large, Specifically, the heart function determination unit 140 of this embodiment obtains the aforesaid frequency gradient time-series waveform that the heart rate-related index calculation unit 110 has found through the arithmetic processing of the time-series waveform of the biosignal (RCW) obtained from the biosignal measurement device 1 at the time of the determination of the physical condition, for example, at the time of the determination of the physical condition of a driver in the middle of driving, at the time of the determination of the physical condition of a subject after driving or exercise, or the like. Next, the heart function determination unit 140 frequency-analyzes this frequency-gradient time-series waveform. Then, the frequency analysis result at the time of the physical condition determination is compared with the frequency analysis result of a frequency-gradient time-series waveform found in advance at the resting time (see FIG. 4). If it turns out that a ratio of a power spectrum value of a dominant frequency at the time of the physical condition determination after the exercise load to a power spectrum value of a dominant frequency at the resting time (PSD ratio) is equal to or larger than a predetermined value (for example, 2 or more), it is determined that the load on the heart function is large as illustrated in, for example, FIG. 9. The frequency analysis result at the resting time is data obtained through the analysis of a biosignal measured when the subject has a normal heart rate and breathing state such as when the subject is calmly seated in a chair without undergoing a load of driving, exercise, or the like, and storing this data in advance in the storage unit of the computer constituting the physical condition determination device 100 enables the physical condition sudden change determination unit 130 to read the stored data to use it for the aforesaid comparison at the time of the physical condition determination.

In the case where the physical condition determination device 100 has the heart function determination unit 140, the physical condition sudden change determination unit 130 determines that the physical condition sudden change has occurred, when the aforesaid sign of the sudden change in the heart rate and the aforesaid sign of the sudden change in the blood pressure appear, in consideration of the determination result of the heart function determination unit 140. Specifically, even in the case where the sign of the sudden change in the heart rate and the sign of the sudden change in the blood pressure appear within the aforesaid predetermined time and according to these two indexes, it is determined that the physical condition sudden change has occurred, it is not determined that the physical condition sudden change has occurred if the result that the load on the heart function is small is output by the heart function determination unit 130, and only in the case where the result that the load on the heart function is large is output as well as the two indexes indicate the physical condition sudden change, it is finally determined that the physical condition sudden change has occurred. Therefore, since it is determined that the physical condition sudden change has occurred only when the load on the heart function is large, the determination result that the physical condition sudden change has occurred by the physical condition determination device 100 more matches the occurrence of the physical condition sudden change that the subject is actually conscious of.

EXPERIMENTAL EXAMPLES

Each subject ran on a treadmill for ten minutes to be given an exercise load and how the physical condition after the running changed from that before the running was examined. Before and after given the exercise load, the subject was seated in an automobile seat to whose seat back part the biosignal measurement device 1 was attached, a biosignal of the subject was collected, and the aforesaid physical condition determination device 100 analyzed its data to determine whether or not a physical condition sudden change had occurred. The biosignal for the analysis was a dorsal body surface pulse wave of the vicinity of the second to fourth lumbar vertebrae, and the data was obtained from the acoustic sensor 21 of the lower part biosignal detection unit 13 of the biosignal measurement device 1. An instantaneous heart rate monitor and a continuous blood pressure monitor were worn by the subject to also measure his/her instantaneous blood pressure and continuous blood pressure.

FIG. 10 to FIG. 15 illustrate the experimental results of the subjects. In FIG. 10 to FIG. 15, the charts (a) each illustrate time-series waveforms of autonomic nervous activity, the charts (b) each illustrate a time-series waveform of the instantaneous heart rate, and the charts (c) each illustrate time-series waveforms of the blood pressures. The charts (d) to (g) in FIG. 10 to FIG. 15 illustrate data resulting from the analysis by the physical condition determination device 100, the charts (d) each illustrating time-series waveforms of average values of peak values and bottom values, the charts (e) each illustrating time-series waveforms of gradients of the peak values and the bottom values, the charts (f) each illustrating a frequency-gradient time-series waveform, and the charts (g) each illustrating time-series waveforms of distribution ratios.

Figure 10:
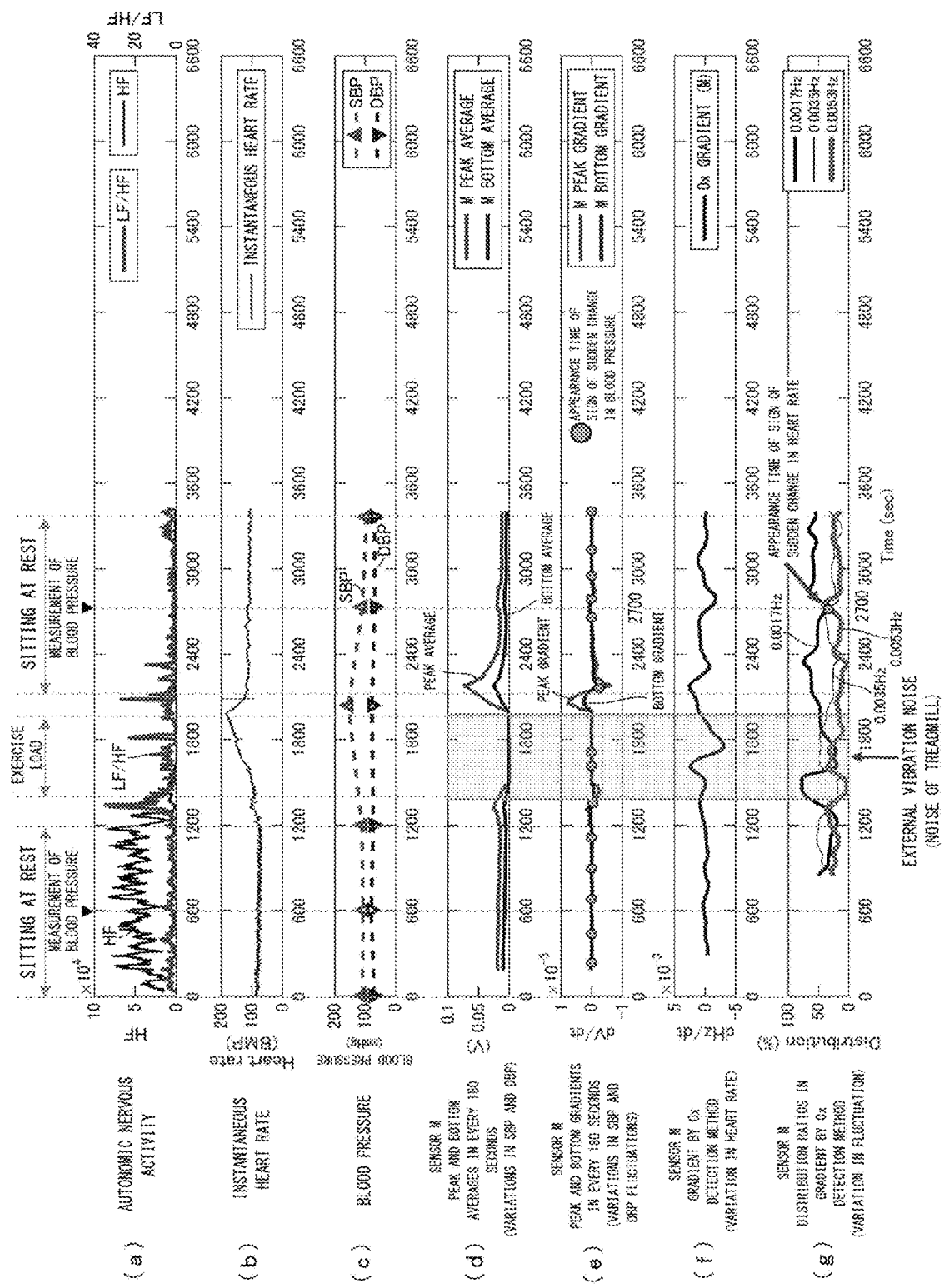
FIGS. 10(a) to (g) are charts illustrating experimental data of a subject O measured on Nov. 13, 2018.

In the data of a subject O measured on Nov. 13, 2018 in FIG. 10, the heart rate sudden change specification unit 131 specifies an around 2700-second point as an appearance time of a sign of a sudden change in heart rate. The blood pressure sudden change specification unit 132 specifies appearance times of sudden change in blood pressure, in 50-second ranges before and after the 2700-second point which is the appearance time of the sign of the sudden change in the heart rate.

Figure 11:
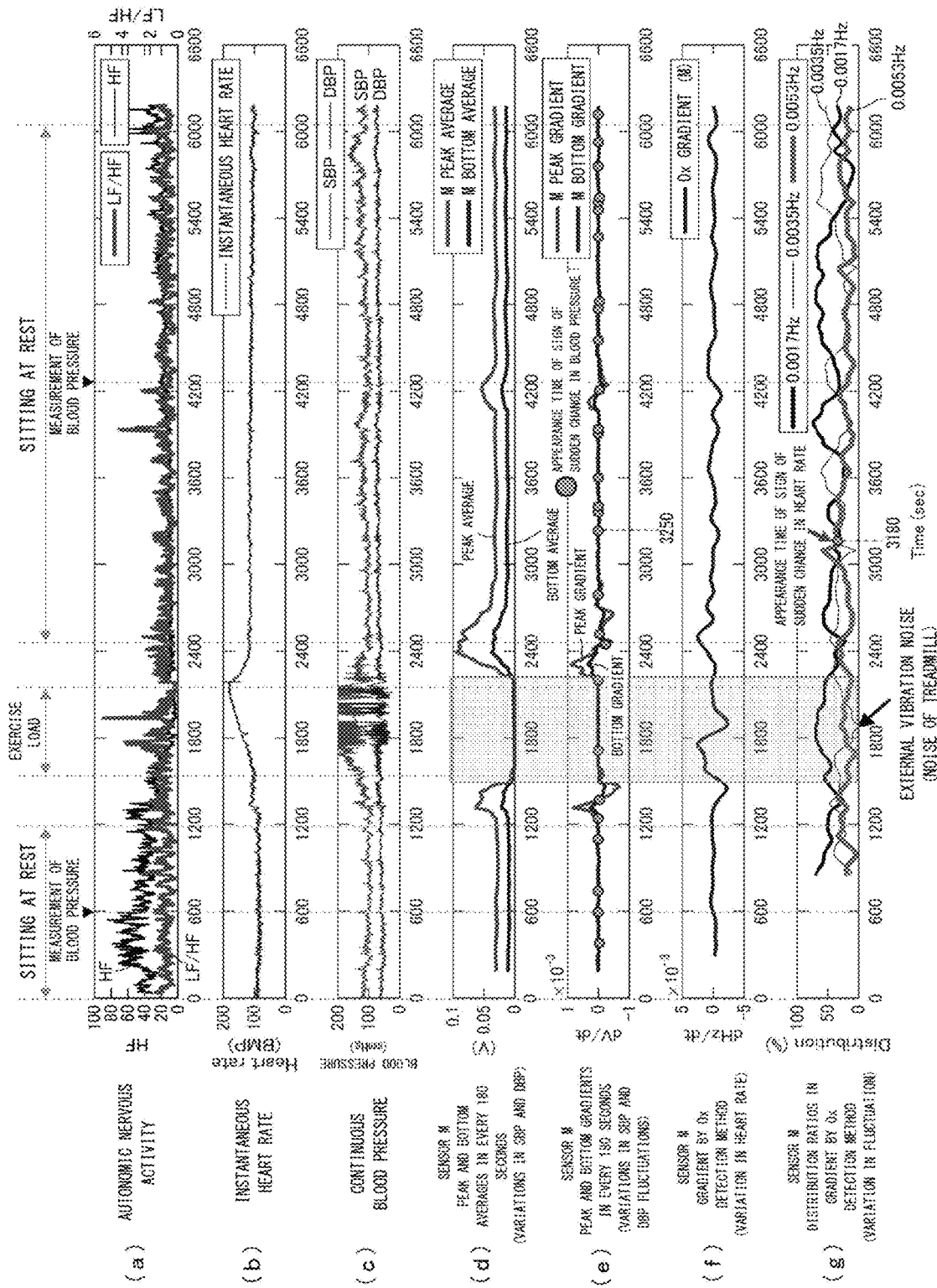
FIGS. 11(a) to (g) are charts illustrating experimental data of the subject O measured on Jan. 18, 2019.
Figure 12:
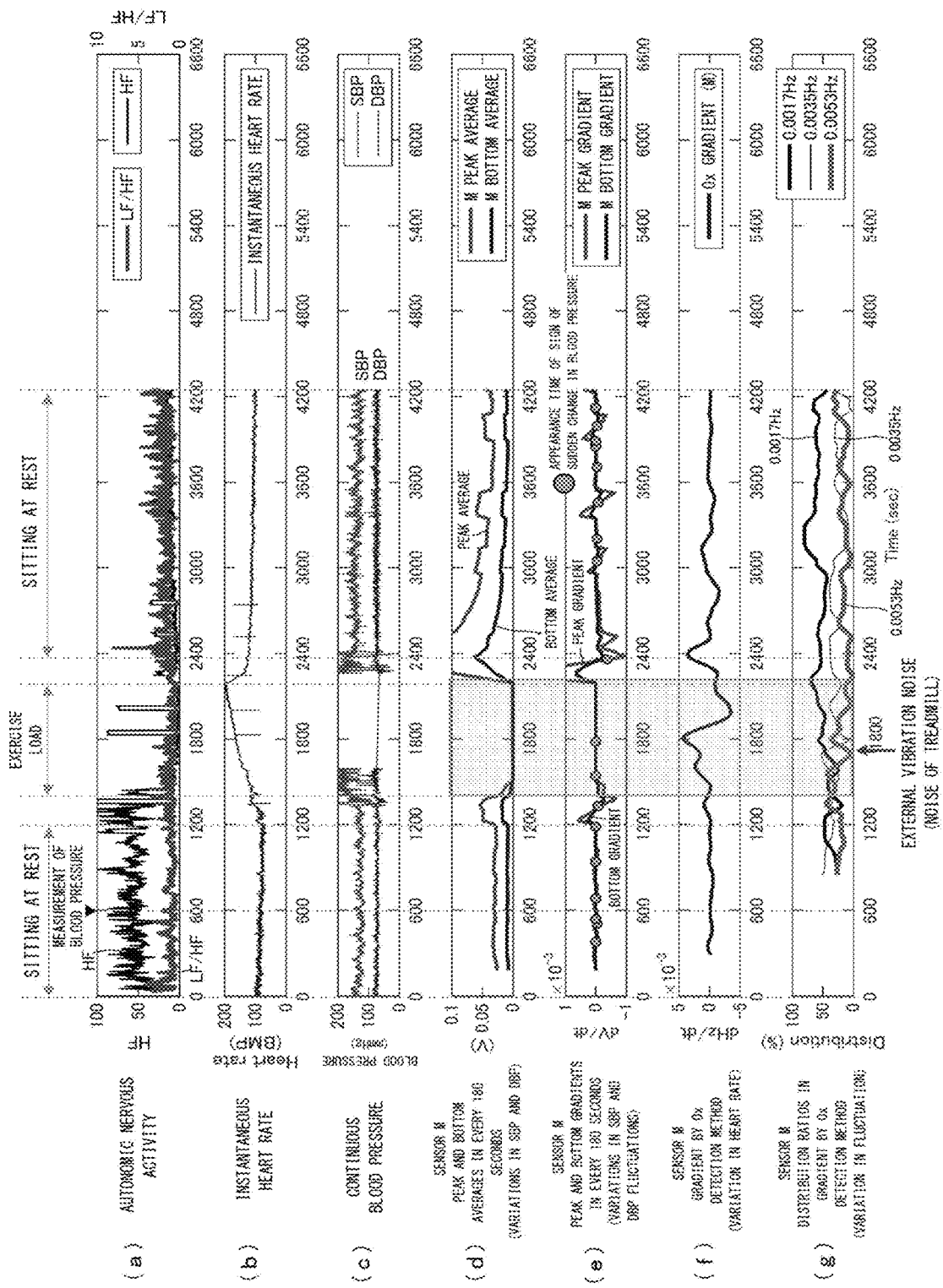
FIGS. 12(a) to (g) are charts illustrating experimental data of a subject U measured on Nov. 14, 2018.
Figure 13:
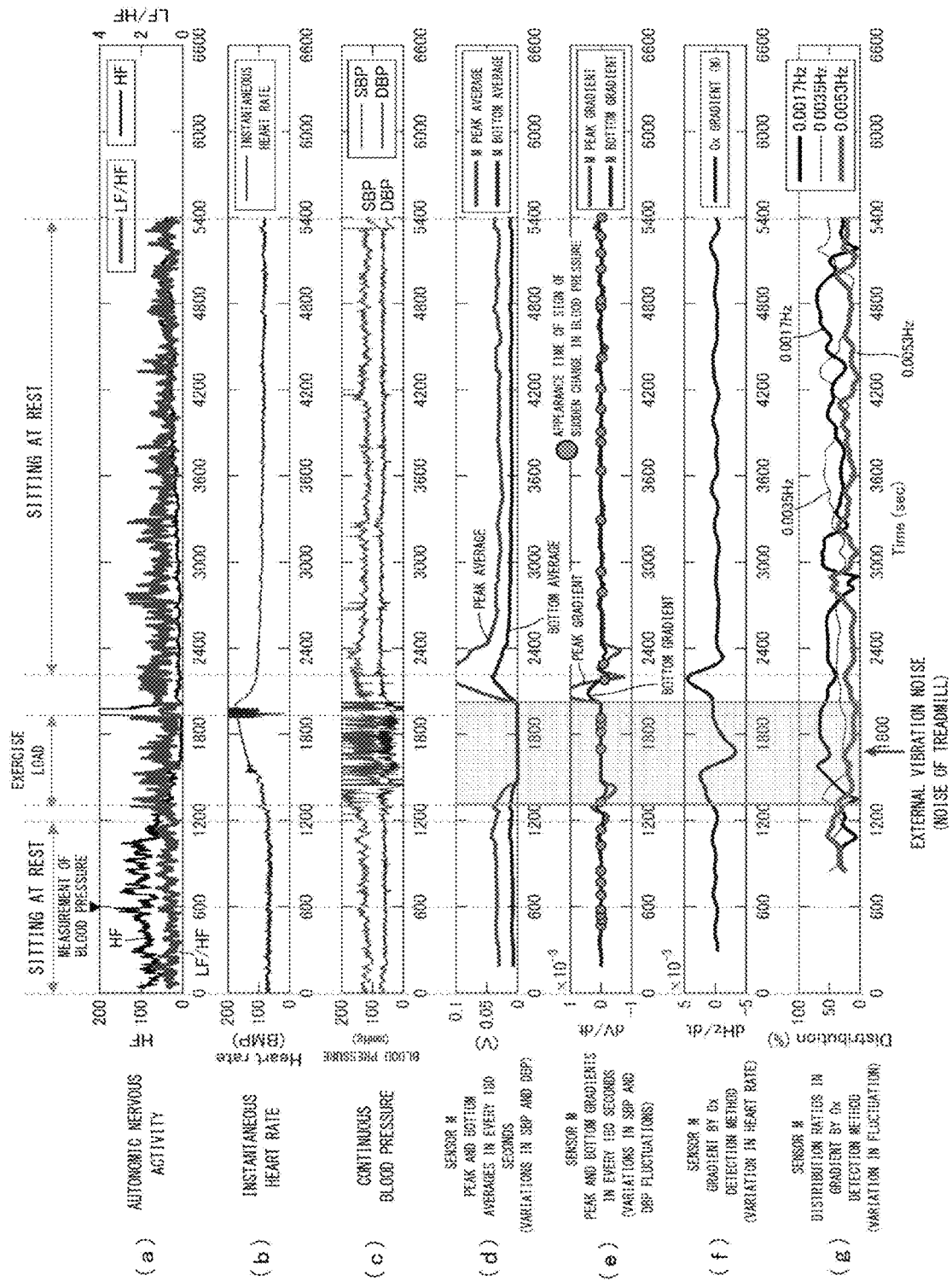
FIGS. 13(a) to (g) are charts illustrating experimental data of a subject H measured on Nov. 20, 2018.
Figure 14:
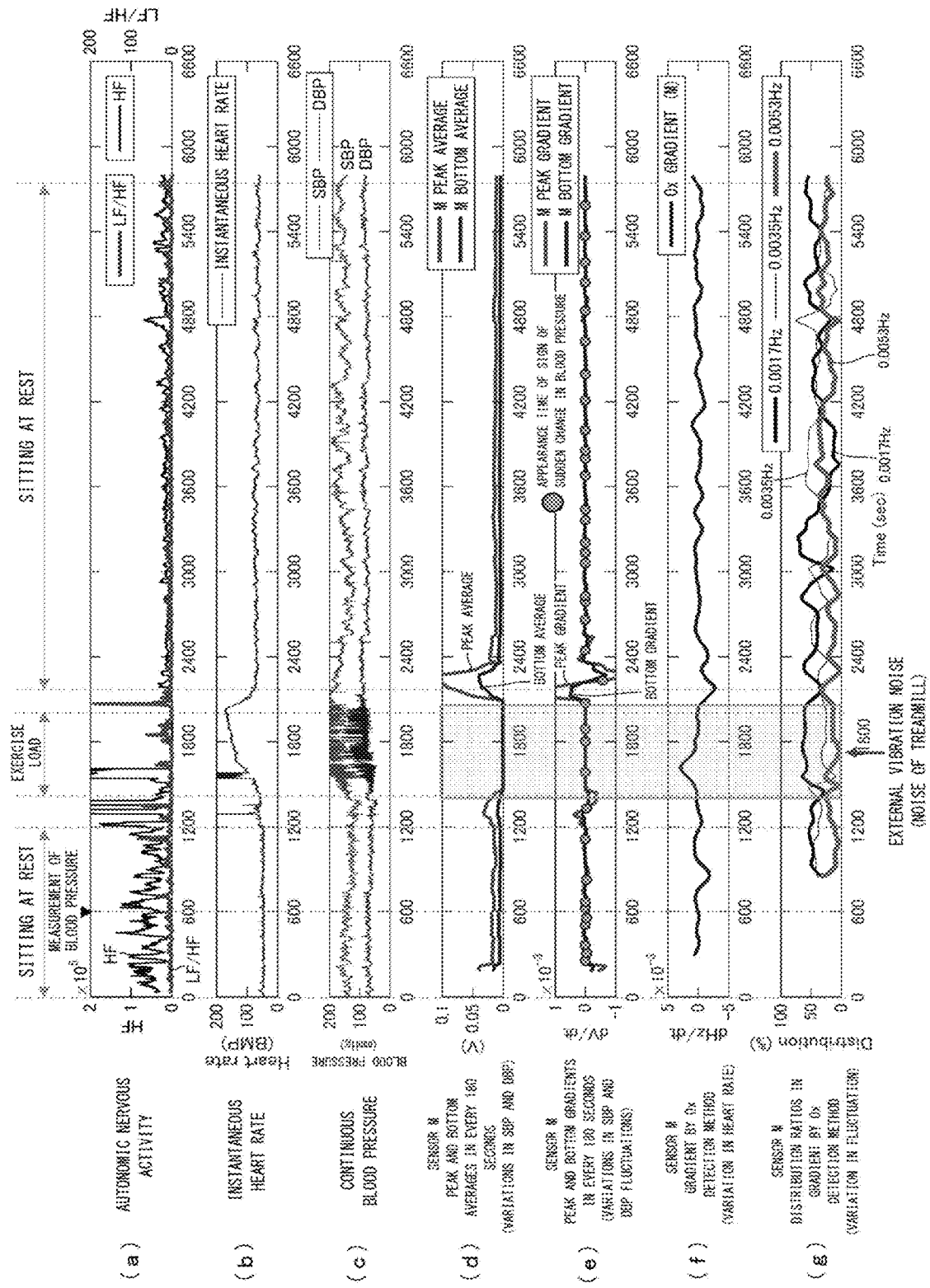
FIGS. 14(a) to (g) are charts illustrating experimental data of a subject MS measured on Dec. 3, 2018.
Figure 15:
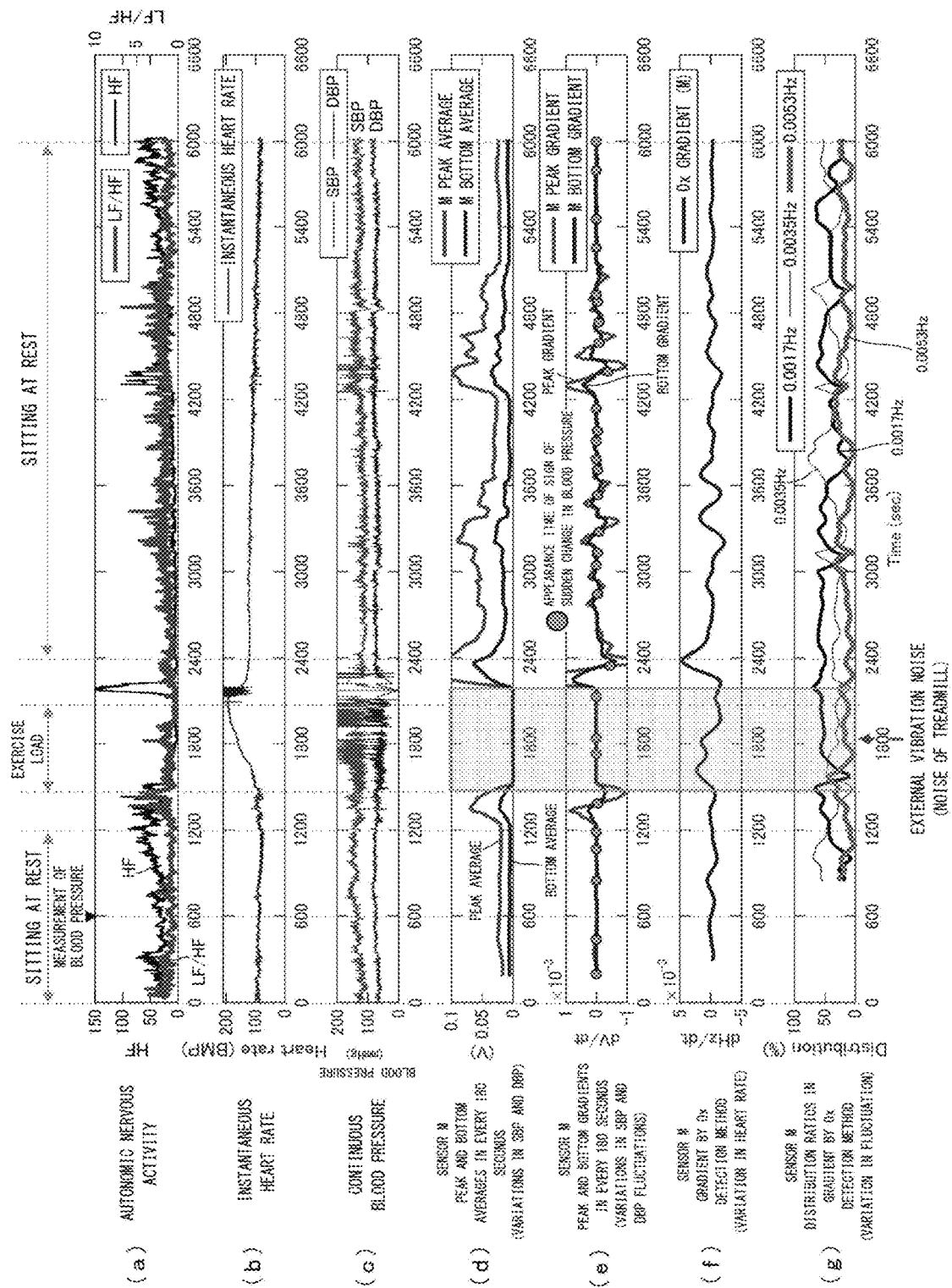
FIGS. 15(a) to (g) are charts illustrating experimental data of a subject MK measured on Dec. 4, 2018.

In the data of the same subject O measured on Jan. 18, 2019 in FIG. 11, the heart rate sudden change specification unit 131 specifies an around 3180-second point as an appearance time of a sign of a sudden change in heart rate. The blood pressure sudden change specification unit 132 specifies an around 3250-second point, as an appearance time of a sign of a sudden change in the blood pressure that is the closest to the appearance time of the sudden change in the heart rate.

In any of the data of subjects U, H, MS, and MK in FIG. 12 to FIG. 15, appearance times of a sudden change in the blood pressure are specified but no appearance time of a sudden change in the heart rate is specified.

In the setting where the determination result of the heart function determination unit 140 is not taken into consideration, the physical condition sudden change determination unit 130 determines that the physical condition sudden change has occurred in the cases of FIG. 10 and FIG. 11 of the subject O in which the appearance time of the sign of the sudden change in the heart rate is specified and near this point, the appearance time of the sign of the sudden change in the blood pressure is specified. On the other hand, in any of the subjects U, H, MS, and MK in FIG. 12 to FIG. 15, the occurrence of a physical condition sudden change is not confirmed.

Figure 16:
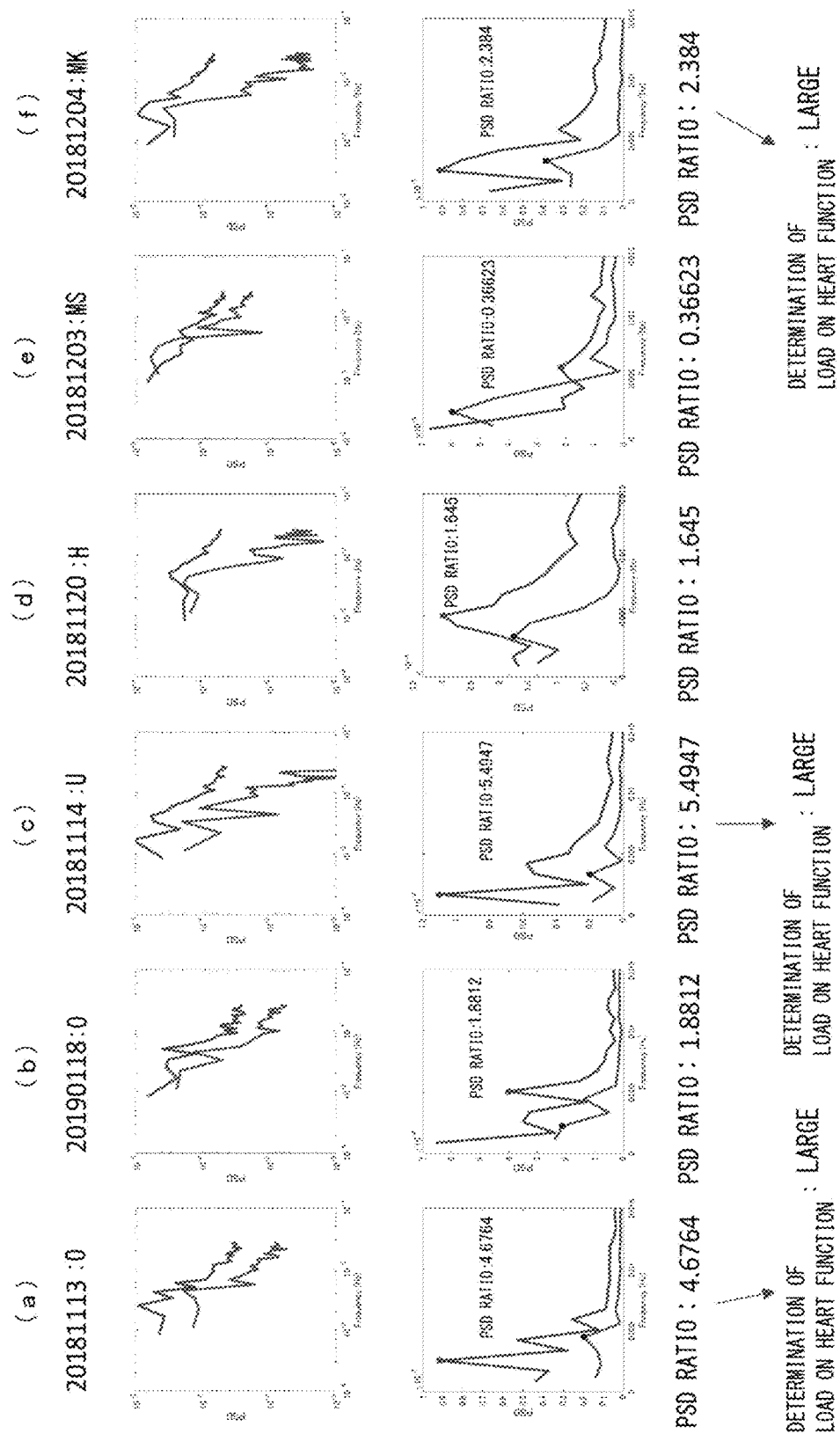
FIGS. 16(a) to (f) are charts illustrating the results of frequency analyses of data at a resting time before an exercise load and data at a resting time after the exercise load in the frequency-gradient time-series waveforms illustrated in FIG. 10(f), FIG. 11(f), FIG. 12(f), FIG. 13(f), FIG. 14(f), and FIG. 15(f), the charts in the lower row being charts where power spectrum values before and after the exercise load are compared, and the charts in the upper row being logarithmic representations of the frequency and the power spectrum value.

FIG. 16 are charts illustrating the results of the determination by the heart function determination unit 140. FIGS. 16(a) to (f) correspond to the data in FIG. 10 to FIG. 15 respectively. The PSD ratios in the charts are found by the heart function determination unit 140 by comparing data in the twenty-minute resting time before the exercise load and data in the twenty-minute resting time after the exercise load, a threshold of the PSD ratio is set to 2, and in the setting here, if the PSD ratio exceeds 2, the determination result is "load on heart function: large". As a result, regarding the data of the subject O on Nov. 13, 2018 in FIG. 10, the data of the subject U in FIG. 12, and the data of the subject MK in FIG. 15, the determination result was "load on heart function: large".

In the setting where the physical condition sudden change determination unit 130 takes the result of the heart function determination unit 140 into consideration, the data of the subject O on Jan. 18, 2019 in FIG. 11 does not satisfy the requirement for the determination that the load on heart function is large, and only the data of the subject O on Nov. 13, 2018 in FIG. 10 satisfies the requirements that the appearance time of the sign of the sudden change in the heart rate and the appearance time of the sign of the sudden change in the blood pressure are within the predetermined time and the load on the heart function is large. From this result, the physical condition sudden change determination unit 130 determines that the physical condition sudden change has occurred only when the data of the subject O on Nov. 13, 2018 in FIG. 10 is measured.

In the case where only the condition that the appearance time of the sign of the sudden change in the heart rate and the appearance time of the sign of the sudden change in the blood pressure are specified in the same period (the predetermined time) serves as a basis of the determination that the physical condition sudden change has occurred, the substantially realtime determination is enabled. This enables the determination of the physical condition sudden change of a driver in the middle of driving. On the other hand, in FIGS. 16(a) to (f), since the heart function is determined using the data in twenty minutes after the exercise load, it requires a certain time to obtain the result regarding whether or not the load on the heart function is large. However, the more accurate determination is enabled if the following configuration is adopted. That is, it is temporarily determined that the physical condition sudden change has occurred when the appearance time of the sign of the sudden change in the heart rate and the appearance time of the sign of the sudden change in the blood pressure are in the same period, and thereafter, in consideration of the result of the determination on whether or not the load on the heart function is large, it is determined again whether or not the physical condition sudden change has occurred. Further, if a time width of the frequency analysis at the time of the determination on whether or not the load on the heart function is large is set short, the load on the heart function can be determined at a shorter interval, and the determination in consideration of the determination result regarding the load on the heart function is enabled at a timing closer to the appearance time of the sign of the sudden change in the heart rate and the appearance time of the sign of the sudden change in the blood pressure.

Actually, when the data of the subject O on Nov. 13, 2018 in FIG. 10 was measured, an observer attending the experiment confirmed that the subject O got pale and underwent such a physical condition sudden change as to momentarily fall unconscious about sixty seconds later from the around 2700-second point at which the appearance time of the sign of the sudden change in the heart rate and the appearance time of the sudden change in the blood pressure were specified. On the other hand, when the data of the subject O on Jan. 18, 2019 in FIG. 11 was measured, the observer confirmed that the subject O had no symptom considered as the physical condition sudden change though the appearance time of the sign of the sudden change in the heart rate and the appearance time of the sign of the sudden change in the blood pressure were specified near a 3200-second point. Therefore, to more accurately determine the physical condition sudden change, the physical condition sudden change determination unit 130 preferably takes the result of the determination by the heart function determination unit 140 into consideration. However, in the data of the subject O on Jan. 18, 2019 in FIG. 11, the appearance time of the sign of the sudden change in the heart rate and the appearance time of the sudden change in the blood pressure are different by about seventy seconds, and therefore, if the predetermined time range in which these signs should appear is set shorter, for example, set to fifty seconds, it is not determined that the physical condition sudden change has occurred, even based only on the criteria of whether the appearance time of the sign of the sudden change in the heart rate and the appearance time of the sign of the sudden change in the blood pressure are within the predetermined time. Therefore, this set time may be adjustable for each individual according to accumulated data of each individual.

Figure 17:
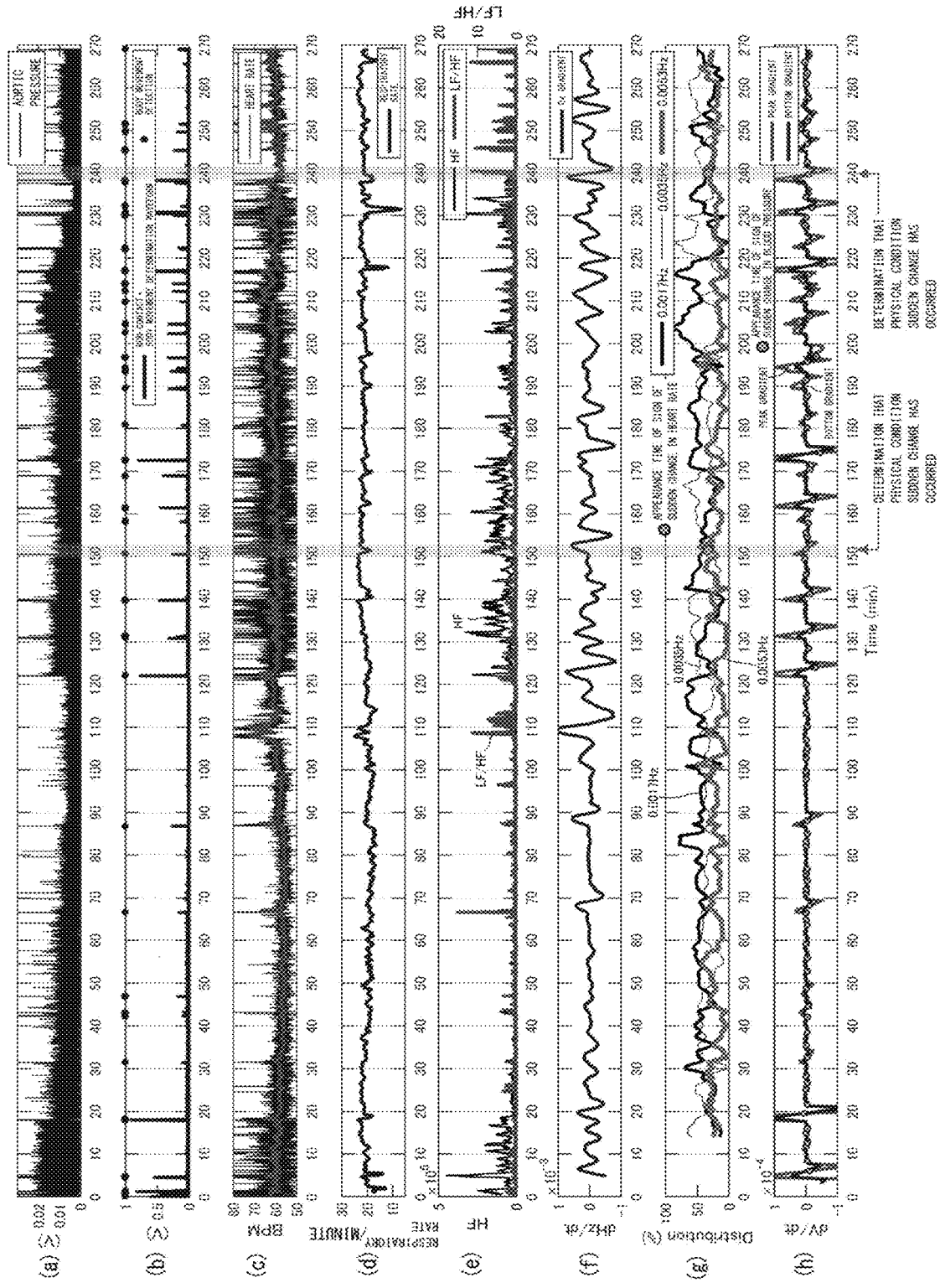
FIGS. 17(a) to (h) illustrate data of the results of experiments that are conducted while the biosignal measurement device 1 is disposed on a mattress and a subject sleep thereon for 270 minutes in a supine posture.

FIG. 17 illustrate data obtained when the biosignal measurement device 1 was placed on a mattress and a subject slept thereon in a supine posture for 270 minutes. FIG. 17(a) is a chart illustrating an aortic pressure waveform resulting from the filtering of a biosignal obtained from the left upper part biosignal detection unit 11, FIG. 17(b) is a chart illustrating the detection timings of body movement and time zones in which the subject is not in contact with the left upper part biosignal detection unit 11 because of the body movement, FIG. 17(c) is a chart illustrating heart rate, FIG. 17(d) is a chart illustrating respiratory rate, FIG. 17(e) is a chart illustrating time-series waveforms of autonomic nervous activity, FIG. 17(f) is a chart illustrating a frequency-gradient time-series waveform, FIG. 17(g) is a chart illustrating time-series waveforms of distribution ratios, and FIG. 17(h) is a chart illustrating time-series waveforms of a peak value gradient and a bottom value gradient.

In FIG. 17(g) and FIG. 17(h), at an about 152-minute point, a sign of a sudden change in heart rate appears and a sign of a sudden change in blood pressure also appears. Similarly, at an about 240-minute point, a sign of a sudden change in the heart rate appears and a sign of a sudden change in the blood pressure also appears. Therefore, during this experiment, at the about 152-minute and 240-minute points, it was determined that a physical condition sudden change had occurred. An observer observed that the subject's body movement momentarily became large and the subject seemed hard to sleep before and after the times at which it was determined that the physical condition sudden change had occurred. From this, it can be said that the determination result by the physical condition determination device 130 was mostly appropriate.

EXPLANATION OF REFERENCE SIGNS 1 biosignal measurement device
13 lower part biosignal detection unit
21 acoustic sensor
100 physical condition determination device
110 heart rate-related index calculation unit
111 frequency-gradient time-series waveform calculation unit
112 distribution ratio calculation unit
120 blood pressure-related index calculation unit
121 systolic blood pressure-related index calculation unit
122 diastolic blood pressure-related index calculation unit
130 physical condition sudden change determination unit
131 heart rate sudden change specification unit
132 blood pressure sudden change specification unit
140 heart function determination unit

The invention claimed is:

1. A physical condition determination device which determines a physical condition of a person by analyzing a biosignal collected by a biosignal measurement device which is disposed in contact with a back of the person and captures, in a non-constraining manner, the biosignal propagated through a body surface of the back, the physical condition determination device comprising:
a heart rate-related index calculation unit which finds a time-series waveform of an index corresponding to a variation in heart rate from a time-series waveform of the biosignal;
a blood pressure-related index calculation unit which finds a time-series waveform of an index corresponding to a variation in blood pressure from the time-series waveform of the biosignal; and
a physical condition sudden change determination unit which specifies a preset time zone in which the time-series waveform obtained from the heart rate-related index calculation unit presents a predetermined waveform variation, as an appearance time of a sign of a sudden change in the heart rate, specifies a preset time zone in which the time-series waveform obtained from the blood pressure-related index calculation unit presents a predetermined waveform variation, as an appearance time of a sign of a sudden change in the blood pressure, and determines that a sudden change in the physical condition has occurred in a case where the appearance time of the sign of the sudden change in the heart rate and the appearance time of the sign of the sudden change in the blood pressure are within a predetermined time range.

2. The physical condition determination device according to claim 1,
wherein the heart rate-related index calculation unit comprises:
a frequency-gradient time-series waveform calculation unit which, after finding a frequency time-series waveform from the time-series waveform of the biosignal, finds a frequency-gradient time-series waveform in every predetermined time range from the frequency time-series waveform; and
a distribution ratio time-series waveform calculation unit which extracts, from the frequency-gradient time-series waveform, frequency components belonging to a ULF band to a VLF band corresponding to a function regulation signal having a frequency lower than a frequency at which a fluctuation characteristic of a cardiocirculatory system changes, a fatigue reception signal higher in frequency than the function regulation signal, and an activity regulation signal higher in frequency than the fatigue reception signal, and finds time-series waveforms of distribution ratios of the frequency components.

3. The physical condition determination device according to claim 2,
wherein the physical condition sudden change determination unit specifies, as the appearance time of the sign of the sudden change in the heart rate, a time zone in which a point appears at which the waveforms of the function regulation signal, the fatigue reception signal, and the activity regulation signal all belong to a predetermined distribution ratio range and the distribution ratio of the activity regulation signal is the lowest, and thereafter a point appears at which the distribution ratio of the activity regulation signal becomes higher than the distribution ratios of the function regulation signal and the fatigue reception signal.

4. The physical condition determination device according to claim 1,
wherein the blood pressure-related index calculation unit comprises:
a systolic blood pressure-related index calculation unit which finds a time-series waveform of a systolic blood pressure-related index by using peak values of the time-series waveform of the biosignal; and
a diastolic blood pressure-related index calculation unit which finds a time-series waveform of a diastolic blood pressure-related index by using bottom values of the time-series waveform of the biosignal.

5. The physical condition determination device according to claim 4,
wherein the systolic blood pressure-related index calculation unit finds the time-series waveform of the systolic blood pressure-related index by using a gradient of the peak values in every predetermined time range,
wherein the diastolic blood pressure-related index calculation unit finds the time-series waveform of the diastolic blood pressure-related index by using a gradient of the bottom values in every predetermined time range, and
wherein the physical condition sudden change determination unit specifies, as the appearance time of the sign of the sudden change in the blood pressure, a time zone in which the time-series waveform of the systolic blood pressure-related index found using the gradient of the peak values in every predetermined time range and the time-series waveform of the diastolic blood pressure-related index found using the gradient of the bottom values in every predetermined time range cross each other and a point appears at which a value of the systolic blood pressure-related index is smaller than a value of the diastolic blood pressure-related index.

6. The physical condition determination device according to claim 2, further comprising
a heart function determination unit which determines whether or not a load on a heart function is large,
wherein the physical condition sudden change determination unit determines that the sudden change in the physical condition has occurred in a case where the heart function determination unit determines that the load on the heart function is large as well as the appearance time of the sign of the sudden change in the heart rate and the appearance time of the sign of the sudden change in the blood pressure are within the predetermined time range.

7. The physical condition determination device according to claim 6,
wherein the heart function determination unit frequency-analyzes the frequency-gradient time-series waveform found at the time of the physical condition determination by the heart rate-related index calculation unit, compares the frequency analysis with a frequency analysis of a frequency-gradient time-series waveform found in advance at a resting time, and determines that the load on the heart function is large in a case where a ratio of a power spectrum value of a dominant frequency at the time of the physical condition determination to a power spectrum value of a dominant frequency at the resting time is equal to a predetermined value or more.

8. A non-transitory medium that contains a computer program causing a computer as a physical condition determination device to execute a procedure for determining a physical condition of a person by analyzing a biosignal obtained from a biosignal measurement device which is disposed in contact with a back of the person and captures the biosignal propagated through a body surface of the back, the computer program causing the computer to execute:

a heart rate-related index calculation procedure for finding a time-series waveform of an index corresponding to a variation in heart rate from a time-series waveform of the biosignal;
a blood pressure-related index calculation procedure for finding a time-series waveform of an index corresponding to a variation in blood pressure from the time-series waveform of the biosignal; and
a physical condition sudden change determination procedure for specifying a preset time zone in which the time-series waveform obtained through the execution of the heart rate-related index calculation procedure presents a predetermined waveform variation, as an appearance time of a sign of a sudden change in the heart rate, specifying a preset time zone in which the time-series waveform obtained through the execution of the blood pressure-related index calculation procedure presents a predetermined waveform variation, as an appearance time of a sign of a sudden change in the blood pressure, and determining that a sudden change in the physical condition has occurred in a case where the appearance time of the sign of the sudden change in the heart rate and the appearance time of the sign of the sudden change in the blood pressure are within a predetermined time range.

9. The non-transitory medium according to claim 8, the computer program causing the computer to further execute a heart function determination procedure for determining whether or not a load on a heart function is large,
wherein, in the physical condition sudden change determination procedure, it is determined that the sudden change in the physical condition has occurred in a case where the load on the heart function is determined as large through the execution of the heart function determination procedure as well as the appearance time of the sign of the sudden change in the heart rate and the appearance time of the sign of the sudden change in the blood pressure are within the predetermined time range.

* * * * *